United States Patent [19]
Endo et al.

[11] Patent Number: 5,866,594
[45] Date of Patent: Feb. 2, 1999

[54] INDOLE-2-CARBOXYLATE DERIVATIVES AND FUNGICIDAL COMPOSITIONS FOR AGRICULTURAL OR HORTICULTURAL USE CONTAINING THE DERIVATIVES AS ACTIVE COMPONENT

[75] Inventors: Yasuhiro Endo; Kan Manabe; Yoshinori Endo; Tomozo Komura; Kazumi Sagayama; Kunio Yamaguchi, all of Tokushima, Japan

[73] Assignee: Otsuka Kagaku Kabushiki Kaisha, Osaka, Japan

[21] Appl. No.: 817,628

[22] PCT Filed: Aug. 1, 1996

[86] PCT No.: PCT/JP96/02170

§ 371 Date: Apr. 4, 1997

§ 102(e) Date: Apr. 4, 1997

[87] PCT Pub. No.: WO97/06141

PCT Pub. Date: Feb. 20, 1997

[30] Foreign Application Priority Data

Aug. 4, 1995 [JP] Japan .................................. 7-199604
Jul. 4, 1996 [JP] Japan .................................. 8-174800

[51] Int. Cl.$^6$ ............................. A01N 43/38; A01N 43/78
[52] U.S. Cl. ........................ 514/367; 514/415; 514/419; 548/159; 548/483; 548/492
[58] Field of Search .................................. 514/415, 419, 514/367

[56] References Cited

U.S. PATENT DOCUMENTS

| | | | |
|---|---|---|---|
| 5,118,695 | 6/1992 | Schleigh et al. | 514/415 X |
| 5,145,845 | 9/1992 | Johnson et al. | 514/419 X |
| 5,229,413 | 7/1993 | Gray et al. | 514/415 |

FOREIGN PATENT DOCUMENTS

| | | |
|---|---|---|
| 60-149502 | 8/1985 | Japan . |
| 64-31762 | 2/1989 | Japan . |
| 93/25524 | 12/1993 | WIPO . |

OTHER PUBLICATIONS

Ainsworth et al., J. Chem. Soc. (C), (10), 1967, 1003–1006.
Ishii et al., Chem. Pharm. Bull., 22(9), 1974, 1981–1989.
Tani et al., Chem. Pharm. Bull., 44(1), 1996, 55–61.
Walser et al., J. Org. Chem., 38(18), 1973, 3077–3084.
Schultz et al., J. Org. Chem., 43(17), 1978, 3391–3393.
Zang et al., Synthesis, Mar. 1996, 377–382.
Chemical Abstract, vol. 53, No. 22, Nov. 25, 1959, Columbus, Ohio, US; Abstract No. 21876e, J. Michalsky, et al., J. Prakt. Chem., vol. 8, 1959, pp. 181–185, Chem. Abs. Registry No. 104115–70–0.
Chemical Abstract, vol. 59, No. 11, Nov. 25, 1963, Columbus, Ohio, US; Abstract No. 12743d, Tsung–Yao Weng, et al., Hua Hsueh Hsueh Pao, vol. 28, No. 2, 1962, pp. 108–113, Chem. Abs. Registry No. 91559–47–6.
Chemical Abstract, vol. 86, No. 3, Jan. 17, 1977, Columbus, Ohio, US; Abstract No. 16941x, G.S. Gadaginamath: Curr. Sci., vol. 45, No. 14, 1976, pp. 507–508.
H. Ishii, et al., Yakugaku Zasshi, vol. 90, No. 6, 1970, pp. 724–729, p. 725; example II.
S.P. Hiremath, et al., J. Indian Chem. Soc., vol. 41, No. 5, 1964, pp. 357–361, compounds IIIa, IVa.
Patent Abstracts of Japan, vol. 009, No. 309 (C–318), Abstract of JP 60–149502, Aug. 7, 1985.

*Primary Examiner*—Fiona T. Powers
*Attorney, Agent, or Firm*—Knobbe, Martens, Olson & Bear, LLP

[57] ABSTRACT

An object of the invention is to provide an indole-2-carboxylic acid ester derivative which shows a selectively high fungicidal effect on fungicide-resistant fungi. The indole-2-carboxylic acid ester derivative of the invention is a compound represented by the formula

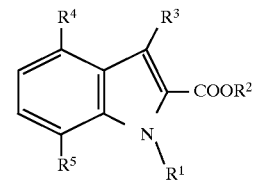

wherein $R^1$ is a hydrogen atom, a hydroxy group, a $C_{1-4}$acyl group, a $C_{1-4}$acyloxy group, a $C_{1-4}$alkoxy group, a ($C_{1-4}$alkoxycarbonyl)oxy group, a phenoxycarbonyl group or a $C_{1-4}$alkoxycarbonyl group, $R^2$ is a $C_{1-4}$alkyl group, $R^3$ is a hydrogen atom, a $C_{1-4}$alkyl group, a $C_{2-4}$alkenyl group, a phenyl group, a cyano group, a carbamoyl group or the like, $R^4$ and $R^5$ are the same or different and each represents $C_{1-4}$alkyl group or a halogen atom.

8 Claims, No Drawings

INDOLE-2-CARBOXYLATE DERIVATIVES AND FUNGICIDAL COMPOSITIONS FOR AGRICULTURAL OR HORTICULTURAL USE CONTAINING THE DERIVATIVES AS ACTIVE COMPONENT

This application is a 371 of PCT/JP96/02170 filed Aug. 1, 1996.

TECHNICAL FIELD

The present invention relates to indole-2-carboxylate derivatives and a fungicidal composition for agricultural or horticultural use which contains the derivative as an active component.

Background Art

Various fungicides have been used in growing agricultural or horticultural crops to prevent the disease of crops, but have not always been satisfactory because of the low effects of fungicides, their limited effects due to the advent of fungicide-resistant fungi, their phytotoxicity, their pollution of plants and their high toxicity to humans, beasts and fishes.

So far some compounds analogous to the indole-2-carboxylate derivatives of the present invention have been known. For example, Japanese Unexamined Patent Publication No. 149,502/1985 discloses a compound (A) and a compound (B) as shown below which are useful as an intermediate for preparing a fungicidal agent for agricultural or horticultural use:

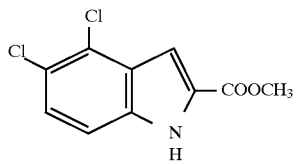

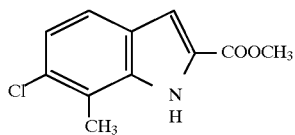

However, the publication made no report on the fungicidal activity of these compounds in agricultural and horticultural use. Japanese Examined Patent Publication No. 65,008/1994 discloses a compound (C) and a compound (D) as shown below which have an activity of preventing deposition of oceanic organisms:

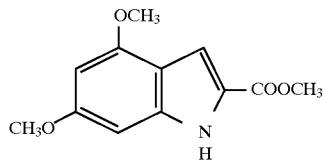

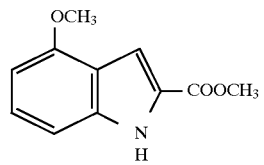

Yet, no report is found in the publication on fungicides for agricultural or horticultural use. Further, J. Heterocyclic Chem., 18, 1373 (1981) reported a compound (E) as shown below which has substituents both at the 4- and 7-positions of the indole ring but mentioned nothing about the fungicidal activity of the compound:

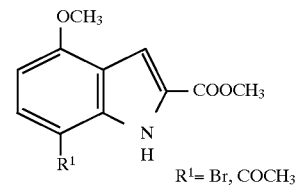

Benzimidazole.thiophanate fungicides as described below have showed a potent effect in controlling pathogenic fungi which are parasitic on agricultural or horticultural crops. Thus, these fungicides have been widely used in agricultural or horticultural fields since about 1970, greatly contributing to the increase in the harvest of crops:

methyl 1-(butylcarbamoyl)benzimidazol-2-yl-carbamate (trade name: "BENOMYL"), 2-(2-furyl)benzimidazole (trade name "FUVERIDAZOLE"), 2-(4-thiazolyl) benzimidazole (trade name "THIABENDAZOLE"), methyl benzimidazol-2-yl-carbamate (trade name "CARBENDAZIM"), 1,2-bis [3-methoxycarbonyl-2-thioureido)benzene (trade name "THIOPHANATE-METHYL"), 1,2-bis(ethoxycarbonyl-2-thioureido)benzene (trade name "THIOPHANATE"), etc. However, these fungicides have showed so reduced fungicidal effects when continuously applied to crops that they often have become inapplicable in practice. If a fungicide applied to plants fails to achieve the desired effect and is unable to prevent the onset of a disease, the user of the fungicide, namely a farmer or the like, would be seriously damaged. Microorganisms which are resistant to any of benzimidazole.thiophanate fungicides are known to become resistant to other fungicides of this group and to exhibit the so-called cross resistance. Consequently, in a farm wherein, for example, BENOMYL is not effective in controlling fungi, other benzimidazole.thiophanate fungicides are not expected to show a fungicidal effect. While the use of benzimidazole.thiophanate fungicides is unavoidably stopped in a farm infested with fungicide-resistant microorganisms, there are many cases known wherein even if the use of a fungicide is discontinued, the density of fungicide-resistant microorganisms has not been reduced. Once fungicide-resistant microorganisms has bred, the farm would remain affected for a prolonged time. In such farm, attempts have been made to prevent the disease of plants by the application of other type of fungicides which do not show cross resistance. Yet only a very few types of fungicides are available which show the same degree of fungicidal effect as benzimidazole.thiophanate fungicides and it is difficult to properly control the fungi.

DISCLOSURE OF THE INVENTION

Since a fungicide which gives a selective fungicidal effect on fungicide-resistant fungi is expected to produce a high fungicidal effect in a farm infested with fungicide-resistant fungi, the inventors of the present invention, considering the foregoing situation, made utmost efforts to develop a fungicide having such a fungicidal ability. The finding was that indole-2-carboxylic acid ester derivatives represented by the following formula (1) shows a selectively high fungicidal effect on fungicide-resistant fungi. The present invention was completed based on this finding.

An object of the present invention is to provide an indole-2-carboxylic acid ester derivative represented by the formula

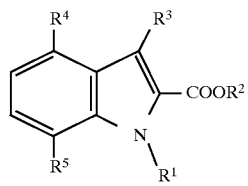

(1)

wherein $R^1$ is a hydrogen atom, a hydroxy group, a $C_{1-4}$acyl group, a $C_{1-4}$acyloxy group, a $C_{1-4}$alkoxy group, a ($C_{1-4}$alkoxycarbonyl)oxy group, a phenoxycarbonyl group or a $C_{1-4}$alkoxycarbonyl group, $R^2$ is a $C_{1-4}$alkyl group, $R^3$ is a hydrogen atom, a $C_{1-4}$alkyl group, a $C_{2-4}$alkenyl group, a phenyl group, a cyano group, a carbamoyl group, a formyl group, a $C_{1-4}$acyl group, a carboxyl group, a $C_{1-4}$alkoxycarbonyl group, a hydroxyiminomethyl group, a ($C_{1-4}$alkoxyimino)methyl group, a ($C_{2-4}$alkynyloxyimino) methyl group, a ($C_{1-4}$acyloxyimino)methyl group, a (N-phenylimino)methyl group, a (N-$C_{1-4}$alkylimino)methyl group, a (N-benzylimino)methyl group, an aminomethyl group, a (($C_{1-4}$alkylthio)thiocarbonyl)aminomethyl group, a ($C_{1-4}$alkylthio)thiocarbonyl group, a nitro group, an amino group, a $C_{1-4}$acylamino group, a 3-($C_{1-4}$alkyl)ureido group, a ($C_{1-4}$alkoxycarbonyl)amino group, a hydroxymethyl group, a ($C_{1-4}$acyloxy)methyl group, a halogen atom, a 2-($C_{1-4}$alkoxycarbonyl)vinyl group, a 2-($C_{1-4}$alkoxycarbonyl)ethyl group, a benzothiazol-2-yl group, a ($C_{1-4}$alkylsulfenyl group, a $C_{1-4}$alkylsulfinyl group, a ($C_{1-4}$alkylsulfonyl group, a phenylsulfenyl group, a phenylsulfinyl group or a phenylsulfonyl group, $R^4$ and $R^5$ are the same or different and each represents a halogen atom, a $C_{1-4}$alkyl group, a $C_{1-4}$alkoxy group, a $C_{1-4}$haloalkyl group, a $C_{1-4}$haloalkoxy group, a benzyl group, a phenyl group, a cyano group, a nitro group, a ($C_{1-4}$alkylsulfenyl group or a $C_{1-4}$alkylsulfonyl group, provided that when $R^1$ is a hydrogen atom, $R^3$ is a hydrogen atom, and $R^4$ is a methoxy group, $R^5$ must not be a bromine atom.

Another object of the invention is to provide a fungicidal composition containing the indole-2-carboxylic acid ester derivative of the formula (1) as an active component.

The compound of the formula (1) according to the invention exhibits a high fungicidal effect on fungicide-resistant microorganisms as apparent from test examples to be described later, and therefore can produce a potent effect of inhibiting the onset of a disease due to fungicide-resistant microorganisms.

The compound of the formula (1) according to the invention neither damages nor pollutes plants, and has a low toxicity to men, beasts and fishes.

The compounds of the formula (1) according to the invention include a compound represented by the following formula (1-a) and a compound represented by the following formula (1-b)

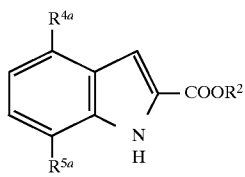

(1-a)

wherein $R^2$ is as defined above, $R^{4a}$ and $R^{5a}$ are the same or different, and each represents a halogen atom, a $C_{1-4}$alkyl group, a $C_{1-4}$alkoxy group, a $C_{1-4}$haloalkyl group, a $C_{1-4}$haloalkoxy group, a benzyl group, a phenyl group, a cyano group, a nitro group, a $C_{1-4}$alkylsulfenyl group or a $C_{1-4}$alkylsulfonyl group, provided that when $R^{4a}$ is a methoxy group, $R^{5a}$ must not be a bromine atom;

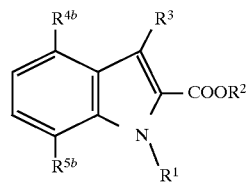

(1-b)

wherein $R^1$, $R^2$ and $R^3$ are as defined above, $R^{4b}$ and $R^{5b}$ are the same or different, and each represents a halogen atom or a $C_{1-4}$alkyl group, provided that when $R^1$ is a hydrogen atom, $R^3$ must not be a hydrogen atom.

Specific examples of groups in the formula (1) are as follows.

Examples of the $C_{1-4}$acyl group are acetyl, propionyl, n-butyryl, isobutyryl, etc.

Examples of the $C_{1-4}$acyloxy group are acetyloxy, propionyloxy, n-butyryloxy, isobutyryloxy, etc.

Examples of the $C_{1-4}$alkoxy group are methoxy, ethoxy, n-propoxy, isopropoxy, n-butoxy, isobutoxy, sec-butoxy, tert-butoxy, etc.

Examples of the ($C_{1-4}$alkoxycarbonyl)oxy group are (methoxycarbonyl)oxy, (ethoxycarbonyl)oxy, (n-propoxycarbonyl)oxy, (isopropoxycarbonyl)oxy, (n-butoxycarbonyl)oxy, (isobutoxycarbonyl)oxy, (sec-butoxycarbonyl)oxy, (tert-butoxycarbonyl)oxy, etc.

Examples of the $C_{1-4}$alkoxycarbonyl group are methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, etc.

Examples of the $C_{1-4}$alkyl group are methyl, ethyl, n-propyl, isopropyl, n-butyl, sec-butyl, tert-butyl, etc.

Examples of the ($C_{1-4}$alkenyl group are vinyl, allyl, isopropenyl, 2-butenyl, 3-butenyl, etc.

Examples of the (($C_{1-4}$alkoxyimino)methyl group are (methoxyimino)methyl, (ethoxyimino)methyl, (n-propoxyimino)methyl, (isopropoxyimino)methyl, (butoxyimino)methyl, etc.

Examples of the ($C_{2-4}$alkynyloxyimino)methyl group are (propargyloxyimino)methyl, (2-butynyloxyimino)methyl, (3-butynyloxyimino)methyl, etc.

Examples of the ($C_{1-4}$acyloxyimino)methyl group are (acetyloxyimino)methyl, (propionyloxyimino)methyl, (n-butyryloxyimino)methyl, (isobutyryloxyimino)methyl, etc.

Examples of the (N-$C_{1-4}$alkylimino)methyl group are (N-methylimino)methyl, (N-ethylimino)methyl, (N-n-propylimino)methyl, (N-isopropylimino)methyl, (N-n-butylimino)methyl, (N-sec-butylimino)methyl, (N-tert-butylimino)methyl, etc.

Examples of the (($C_{1-4}$alkylthio)thio-carbonyl) aminomethyl group are ((methylthio)thiocarbonyl)-aminomethyl, ((ethylthio)thiocarbonyl)aminomethyl, ((n-propylthio)thiocarbonyl)aminomethyl, ((isobutylthio) thiocarbonyl)aminomethyl, ((sec-butylthio)thiocarbonyl) aminomethyl, ((tert-butylthio)thiocarbonyl)aminomethyl, etc.

Examples of the ($C_{1-4}$alkylthio)thiocarbonyl group are (methylthio)thiocarbonyl, (ethylthio)thiocarbonyl, (n-propylthio)thiocarbonyl, (isopropylthio)thiocarbonyl, (n-butylthio)thiocarbonyl, (isobutylthio)thiocarbonyl, (sec-butylthio)thiocarbonyl, (tert-butylthio)thiocarbonyl, etc.

Examples of the $C_{1-4}$acylamino group are acetylamino, propionylamino, n-butyrylamino, isobutyrylamino, etc.

Examples of the 3-($C_{1-4}$alkyl)ureido group are 3-methylureido, 3-ethylureido, 3-(n-propyl)ureido, 3-(isopropyl)ureido, 3-(n-butyl)ureido, 3-(isobutyl)ureido, 3-(sec-butyl)ureido, 3-(tert-butyl)ureido, etc.

Examples of the ($C_{1-4}$alkoxycarbonyl)amino group are (methoxycarbonyl)amino, (ethoxycarbonyl)amino, (isopropoxycarbonyl)amino, (n-butoxycarbonyl)amino, (tert-butoxycarbonyl)amino, etc.

Examples of the ($C_{1-4}$acyloxy)methyl group are (acetoxy)methyl, (propionyloxy)methyl, (n-butyryloxy)methyl, (isobutyryloxy)methyl, etc.

Examples of the halogen atom are fluorine, chlorine, bromine, iodine, etc.

Examples of the 2-($C_{1-4}$alkoxycarbonyl)vinyl group are 2-(methoxycarbonyl)vinyl, 2-(ethoxycarbonyl)vinyl, 2-(n-propoxycarbonyl)vinyl, 2-(isopropoxycarbonyl)vinyl, 2-(n-butoxycarbonyl)vinyl, 2-(isobutoxycarbonyl)vinyl, 2-(sec-butoxycarbonyl)vinyl, 2-(tert-butoxycarbonyl)vinyl, etc.

Examples of the 2-($C_{1-4}$alkoxycarbonyl)ethyl group are 2-(methoxycarbonyl)ethyl, 2-(ethoxycarbonyl)ethyl, 2-(n-propoxycarbonyl)ethyl, 2-(isopropoxycarbonyl)ethyl, 2-(n-butoxycarbonyl)ethyl, 2-(isobutoxycarbonyl)ethyl, 2-(sec-butoxycarbonyl)ethyl, 2-(tert-butoxycarbonyl)ethyl, etc.

Examples of the $C_{1-4}$alkylsulfenyl group are methylsulfenyl, ethylsulfenyl, n-propylsulfenyl, isopropylsulfenyl, n-butylsulfenyl, isobutylsulfenyl, sec-butylsulfenyl, tert-butylsulfenyl, etc.

Examples of the $C_{1-4}$alkylsulfinyl group are methylsulfinyl, ethylsulfinyl, n-propylsulfinyl, isopropylsulfinyl, n-butylsulfinyl, isobutylsulfinyl, sec-butylsulfinyl, tert-butylsulfinyl, etc.

Examples of the $C_{1-4}$alkylsulfonyl group are methylsulfonyl, ethylsulfonyl, n-propylsulfonyl, isopropylsulfonyl, n-butylsulfonyl, isobutylsulfonyl, sec-butylsulfonyl, tert-butylsulfonyl, etc.

Examples of the $C_{1-4}$haloalkyl group are trifluoromethyl, chloromethyl, fluoromethyl, difluoromethyl, chlorodifluoromethyl, 2-chloroethyl, 2,2,2-trifluoroethyl, 2,2,2-chlorodifluoroethyl, 3-bromopropyl, 3-chloropropyl, 2,3-dichloropropyl, 4-fluorobutyl, 3-chloro-2-methylpropyl, etc.

Examples of the $C_{1-4}$haloalkoxy group are trifluoromethoxy, chloromethoxy, fluoromethoxy, difluoromethoxy, chlorodifluoromethoxy, 2-chloroethoxy, 2,2,2-trifluoroethoxy, 2,2,2-chlorodifluoroethoxy, 3-chloropropoxy, 2,3-dichloropropoxy, 4-fluorobutoxy, 3-chloro-2-methylpropoxy, etc.

The compound of the formula (1) according to the invention is effective in controlling fungicide-resistant fungi in a farm wherein they are supposed to appear or have appeared due to the use of benzimidazole.thiophanate fungicide. The compound of the invention can be suitably used in destroying the fungi which are resistant to, e.g. benzimidazole.thiophanate fungicides or the like. Examples of such fungi are *Podosphaera leucotricha, Venturia inaequalis, Mycosphaerella pomi, Marssonina mali, Sclerotinia mali, Phyllactinia kakicola, Gloeosporium kaki, Sclerotinia cinerea, Cladosporium carpophilumn, Phomopsis sp., Botrytis cinerea, Cercospora viticola, Uncinula necator, Elsinoe ampelina, Glomerella cingulata, Cercospora beticola, Cercospora arachidicola, Cercospola personata, Erysiphe graminis f. sp. hordei, Cercosporella herpotrichoides, Fusarium nivale, Erysiphe graminis f. sp. tritici, Sphaerotheca fuliginea, Mycosphaerella melonis, Solerotinia sclerotiorum, Botrytis cinerea, Cladosporium cucumerinum, Cladosporium fulvum, Botrytis cinerea, Corynespora melongenae, Sphaerotheca humuli, Fusarium oxysporum, Botrytis allii, Sclerotinia sclerotiorum, Cercospora apii, Phaecisariopsis griseola, Sclerotinia sclerotiorum, Botrytis cinerea, Erysiphe cichoracearum, Diplocarpon rosae, Elsione fawcetti, Penicillium italicum, Penicillium digitatum*, etc.

The compound of the formula (1) according to the invention can be prepared by various processes. Typical processes are shown below:

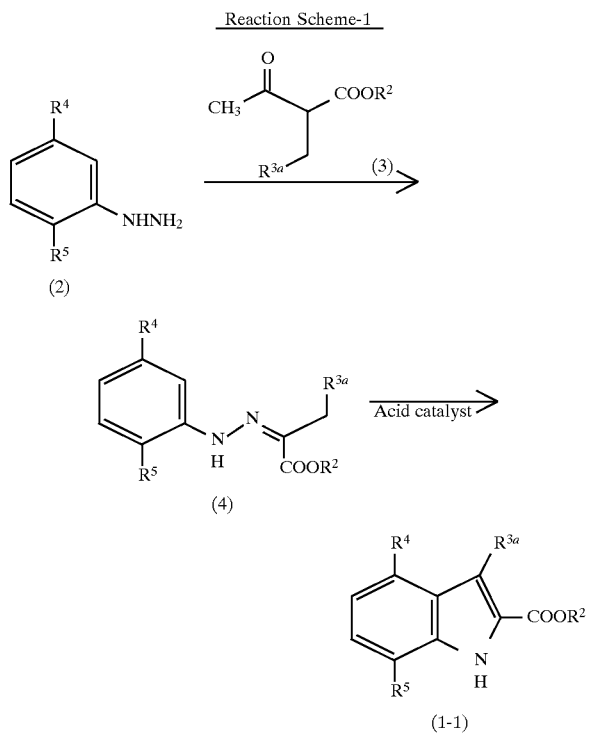

Reaction Scheme-1 wherein $R^2$, $R^4$ and $R^5$ are as defined above, and $R^{3a}$ is a hydrogen atom, a $C_{1-4}$alkyl group or a phenyl group.

According to Reaction Scheme-1, the compound (1-1) of the invention wherein $R^3$ is a hydrogen atom, a $C_{1-4}$alkyl group or a phenyl group can be prepared by reacting a phenylhydrazine of the formula (2) with a compound of the formula (3) in the presence of a suitable catalyst to give a hydrazone compound of the formula (4) and heating the compound of the formula (4) in a suitable solvent in the presence of an acid catalyst.

The reaction of the phenylhydrazine of the formula (2) with the compound of the formula (3) can be conducted usually in the presence of a suitable solvent. Useful solvents are, for example, methanol, ethanol and like alcohols, benzene, toluene, xylene and like aromatic hydrocarbons, methylene chloride, chloroform and like halogenated hydrocarbons, and mixtures thereof. The catalyst which can be used in the reaction include, for example, Lewis acid and organic acids. Among them, boron trifluoride-etherate and p-toluenesulfonic acid are especially preferred. As to the proportions of the phenylhydrazine of the formula (2) and the catalyst, about 0.001 to about 0.1 mole, preferably about 0.01 to about 0.05 mole, of the latter is used per mole of the former. As to the proportions of the phenylhydrazine of the formula (2) and the compound of the formula (3), about 0.5 to about 2 moles, preferably about 1 to about 1.2 moles, of the latter is used per mole of the former. The reaction can proceed at a temperature ranging from room temperature to the boiling point of the solvent to be used, preferably a temperature in the vicinity of the boiling point of the solvent to be used. The reaction is completed usually in about 1 to about 6 hours.

The reaction for producing the compound (1-1) of the invention from the hydrazone compound of the formula (4) can be carried out with a suitable solvent or without a solvent in the presence of an acid catalyst. Useful acid catalysts include, for example, polyphosphoric acid, phosphoric acid and like phosphoric acids, acetic acid, propionic acid and like organic acids, zinc chloride, stannic chloride and like Lewis acids, and so on. Among useful solvents, preferred are, for example, aromatic hydrocarbons such as toluene and xylene, and glycol ethers such as dimethoxyethane and diethylene glycol. The heating temperature is usually 100° to 300° C., preferably 150° to 200° C. The heating time is in the range of about 30 minutes to about 2 hours.

The phenylhydrazine of the formula (2) to be used as one of the raw materials in Reaction Scheme-1 may be a commercially available compound or can be easily prepared according to conventional methods, for example, by subjecting the corresponding aniline to diazotization and to reduction. The method is described in detail, for example, in Beilstein, 15, 468.

The compound of the formula (3) to be used as one of the raw materials in Reaction Scheme-1 can be easily produced in accordance with conventional methods, e.g. the method disclosed in Chem. Ber., 21, 549 (1888).

Reaction Scheme-2

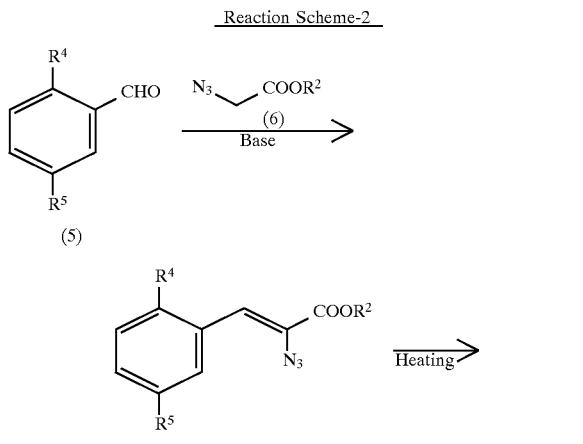

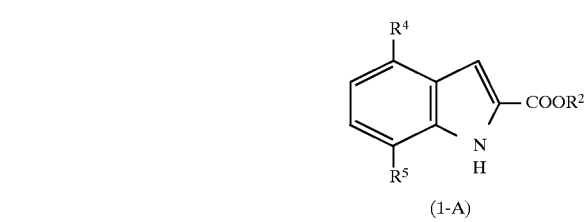

wherein $R^2$, $R^4$ and $R^5$ are as defined above.

According to Reaction Scheme-2, the compound (1-A) of the invention (the compound (1-1) wherein $R^{3a}$ is a hydrogen atom) can be prepared by reacting an aldehyde of the formula (5) with an azidoacetic acid ester of the formula (6) in a suitable base to give a cinnamate compound of the formula (7) and heating the compound of the formula (7).

The reaction between the aldehyde of the formula (5) and the azidoacetic acid ester of the formula (6) can be conducted usually in a suitable solvent. Examples of useful solvents are methanol, ethanol and like alcohols, benzene, toluene, xylene and like aromatic hydrocarbons, acetonitrile, propionitrile and like nitriles, etc. Useful bases include, for example, sodium methoxide, sodium ethoxide, sodium t-butoxide, potassium t-butoxide and like alkoxides of alkali metals, sodium carbonate, potassium carbonate and like anhydrous carbonates of alkali metals, etc. As to the proportions of the compound of the formula (5) and the base, about 0.5 to about 10 moles, preferably about 1 to about 3 moles, of the latter is used per mole of the former. As to the proportions of the compound of the formula (5) and the azidoacetic acid ester of the formula (6), about 0.5 to about 10 moles, preferably about 2 to about 5 moles, of the latter is used per mole of the former. The reaction can proceed at a temperature ranging from −40° C. to the boiling point of the solvent to be used, preferably from −20° C. to room temperature. The reaction is completed usually in about 1 to about 6 hours.

The compound of the formula (5) to be used as one of the raw materials in the above reaction may be a commercially available compound or can be easily prepared from the corresponding carboxylic acid or aldehyde as described in detail, for example, in Tetrahedron, 42 (12), 3259 (1986). The azidoacetic acid ester of the formula (6) useful as one of the raw materials can be easily prepared from sodium azide and halogeno-acetic acid ester according to conventional methods such as the method described in detail in Synthesis, 823 (1976).

The reaction for producing the compound (1-A) of the invention from the cinnamate compound of the formula (7) can proceed by heating the compound (7) in a suitable solvent. A wide variety of conventional solvents can be used for this purpose. Preferred solvents are benzene, toluene, xylene and like hydrocarbons. The reaction temperature is the boiling point or nearly that of the solvent to be used, preferably 100° to 200° C. The reaction is completed usually in about 1 to about 5 hours.

Reaction Scheme-3

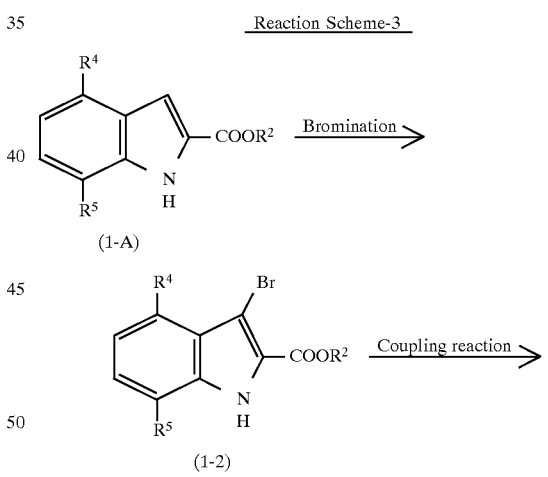

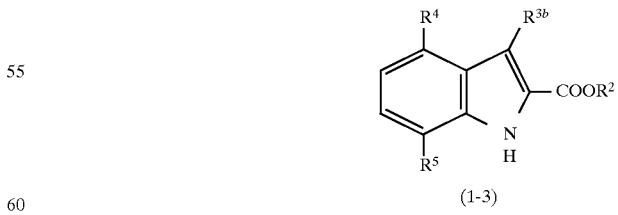

wherein $R^2$, $R^4$ and $R^5$ are as defined above and $R^{3b}$ is a $C_{2-4}$ alkenyl group or a phenyl group.

According to Reaction Scheme-3, the compound (1-2) of the invention wherein $R^3$ is a bromine atom can be prepared by bromination of the compound (1-A) of the invention. The compound (1-3) of the invention wherein $R^3$ is a $C_{2-4}$ alkenyl group or a phenyl group can be prepared by reacting the above-obtained compound (1-2) of the invention with allyl acetate or like alkenyl acetate or phenylboric acid in the presence of a suitable coupling catalyst.

The compound (1-A) of the invention can be easily brominated by conventional methods, e.g. the method disclosed in Heterocycles, 34, 2349 (1992).

The reaction for producing the compound (1-3) of the invention from the compound (1-2) of the invention can be carried out according to conventional methods, e.g. the methods described in J. Org. Chem., 56, 3763 (1991) and Tetrahedron Lett., 1985, 6457 or Heterocycles, 31, 1505 (1990).

Reaction Scheme-4

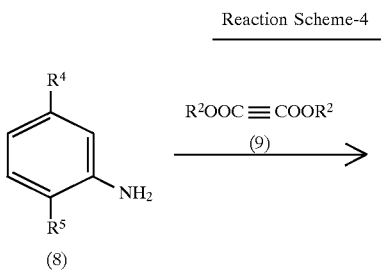

-continued
Reaction Scheme-4

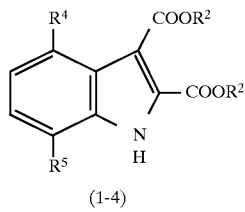

(1-4)

wherein $R^2$, $R^4$ and $R^5$ are as defined above.

According to Reaction Scheme-4, the compound (1-4) of the invention wherein $R^3$ is a $C_{1-4}$alkoxycarbonyl group can be prepared by reacting an aniline of the formula (8) with an alkylenedicarboxylic acid ester of the formula (9) to give a diester of the formula (10) and subjecting the diester of the formula (10) to a ring-closing reaction in the presence of a suitable catalyst.

The reaction between the aniline of the formula (8) and the alkylenedicarboxylic acid ester of the formula (9) can be easily made by conventional methods, e.g. the method described in Japanese Unexamined Patent Publication No. 116,269/1994.

The ring-closing reaction of the diester of the formula (10) can be easily made by conventional methods, e.g. the method described in Japanese Unexamined Patent Publication No. 122,684/1994.

Reaction Scheme-5

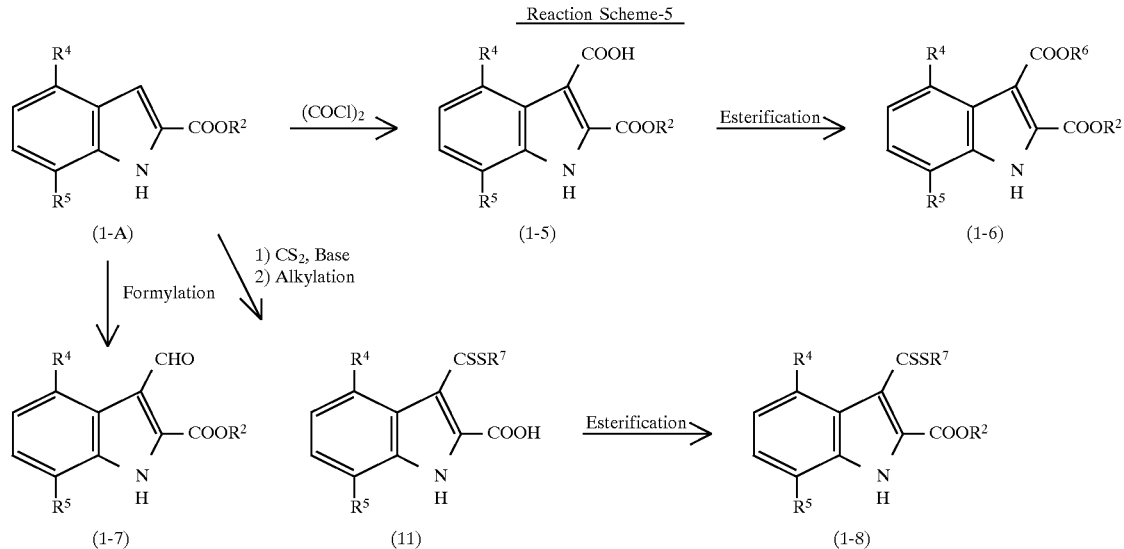

-continued
Reaction Scheme-4

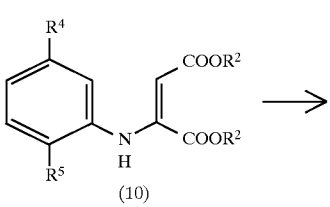

wherein $R^2$, $R^4$ and $R^5$ are as defined above, and $R^6$ and $R^7$ are $C_{1-4}$alkyl groups.

According to Reaction Scheme-5, the compound (1-5) of the invention wherein $R^3$ is a carboxyl group can be prepared by reacting the compound (1-A) of the invention with oxalyl chloride in the presence of an acid catalyst. The compound (1-6) of the invention wherein $R^3$ is a $C_{1-4}$alkoxycarbonyl group can be prepared by esterification of the above-obtained compound (1-5) of the invention.

The reaction between the compound (1-A) of the invention and oxalyl chloride can be made by conventional methods, e.g. the method described in Org. Synth., Coll. Vol. V, 706 (1973).

The compound (1-5) of the invention can be esterified according to methods commonly carried out in the art. The compound (1-6) can be prepared, for example, by reacting the compound (1-5) with an alcohol in an inert solvent in the presence of a condensing agent such as dicyclohexylcarbodiimide (DCC). Optionally the compound (1-6) can be also prepared by reacting the compound (1-5) with a halogenating agent such as thionyl chloride or phosphorus trichloride to give an acyl halide and reacting the acyl halide with an alcohol in the presence of an acid binder. Further optionally, the compound (1-6) can be prepared by reacting the compound (1-5) with diazoalkane such as diazomethane.

According to Reaction Scheme-5, the compound (1-7) of the invention wherein $R^3$ is a formyl group can be prepared by formylation of the compound (1-A) of the invention.

The compound (1-A) of the invention can be easily formylated by conventional methods such as those described in, e.g. Org. Synth., Coll. Vol. IV, 539 (1963) and J. Chem. Soc., Perkin trans. 1, 2895 (1984). Stated more specifically, the formylation can be performed by reacting the compound (1-A) of the invention with a Vilsmeier reagent prepared from N,N-dimethylformamide and phosphoryl chloride.

Further, according to Reaction Scheme-5, the compound (1-8) of the invention wherein $R^3$ is a ($C_{1-4}$alkylthio)thiocarbonyl group can be prepared by reacting the compound (1-A) of the invention with carbon disulfide in the presence of a suitable base, alkylating the resulting reaction product to give 3-(dithioester)indole-2-carboxylic acid of the formula (11) and esterifying the compound of the formula (11).

The reaction for producing the compound of the formula (11) from the compound (1-A) of the invention can be practiced by conventional methods such as the method described in Yakugaku Zasshi, 91, 1164 (1971).

The compound of the formula (11) can be esterified in the same manner as done for the esterification of the compound (1-5) of the invention.

wherein $R^2$, $R^4$ and $R^5$ are as defined above, $R^8$ is a $C_{1-4}$alkyl group, a benzyl group or a phenyl group and $R^9$ is a $C_{1-4}$acyl group, a $C_{1-4}$alkyl group or a $C_{2-4}$alkynyl group.

According to Reaction Scheme-6, the compound (1-9) of the invention wherein $R^3$ is a hydroxyiminomethyl group can be prepared by reacting the compound (1-7) of the invention obtained in Reaction Scheme-5 with hydroxylamine. The compound (1-10) of the invention wherein $R^3$ is a cyano group can be prepared by dehydrating the above-obtained compound (1-9) of the invention.

The reaction between the compound (1-7) of the invention and the hydroxylamine can be made by conventional methods, e.g. by subjecting the compound of the formula (7) and hydroxylamine hydrochloride to condensation reaction in ethanol.

The dehydration reaction of the compound (1-9) of the invention can be easily made properly utilizing conventional methods available in the art, as by treatment of the compound (1-9) of the invention with a dehydrating agent such as thionyl chloride, phosphorus pentoxide or the like in an inert solvent such as toluene, diethyl ether or the like.

According to Reaction Scheme-6, the compound (1-11) of the invention wherein $R^3$ is a (N-phenylimino)methyl group, a (N-$C_{1-4}$alkylimino)methyl group or a (N-benzylimino)methyl group can be prepared by subjecting the compound (1-7) of the invention with an amine of the formula (12) to condensation reaction.

The condensation reaction between the compound (1-7) and the amine of the formula (12) can be easily practiced by conventional methods available in the art, as by a procedure of condensing the compound (1-7) and the amine of the formula (12) in the presence of a suitable base or an acid catalyst.

According to Reaction Scheme-6, the compound (1-12) of the invention wherein $R^3$ is a ($C_{1-4}$alkoxyimino)methyl group, a ($C_{2-4}$alkynyloxyimino)methyl group or a ($C_{1-4}$acyloxyimino)methyl group can be prepared by subjecting the compound (1-7) of the invention with a hydroxylamine of the formula (13) to condensation reaction or by reacting the compound (1-9) of the invention with a halide of the formula (14).

Reaction Scheme-6

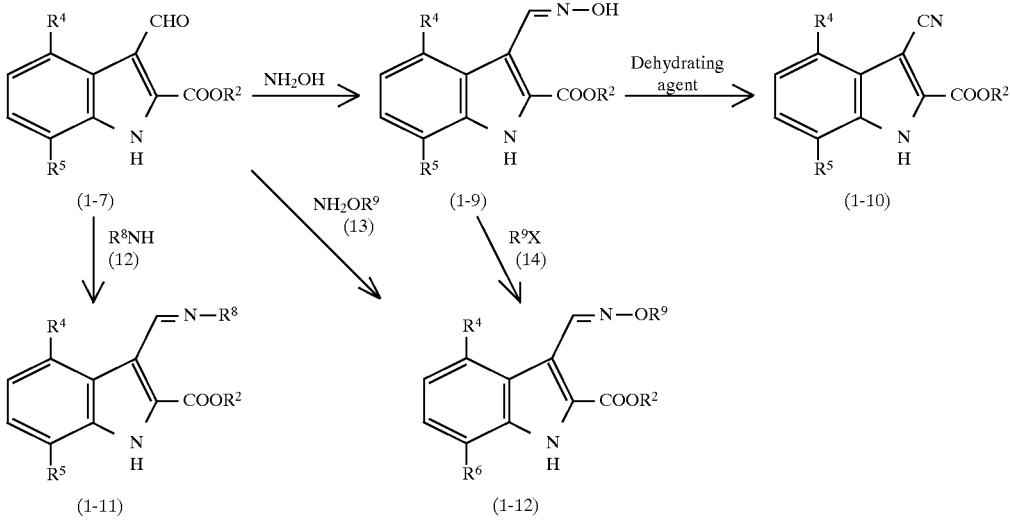

The condensation reaction between the compound (1-7) of the invention and the hydroxylamine of the formula (13) can be performed properly utilizing conventional methods available in the art as in the presence of an acid or a basic catalyst.

The reaction between the compound (1-9) of the invention and the halide of the formula (14) can be made properly utilizing conventional methods available in the art, as in an inert solvent in the presence of an acid binder such as pyridine.

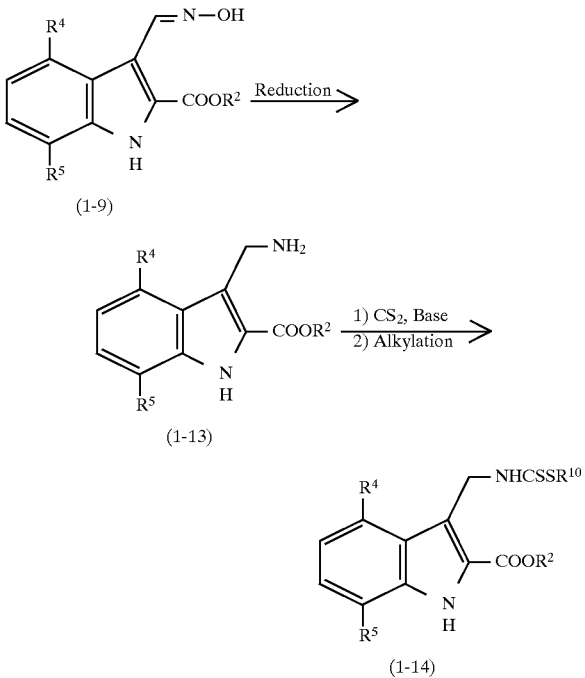

wherein $R^2$, $R^4$ and $R^5$ are as defined above, and $R^{10}$ is a $C_{1-4}$alkyl group.

According to Reaction Scheme-7, the compound (1-13) of the invention wherein $R^3$ is an aminomethyl group can be prepared by reducing the compound (1-9) of the invention obtained in Reaction Scheme-6. The compound (1-14) of the invention wherein $R^3$ is a $((C_{1-4}alkylthio)thiocarbonyl)$-aminomethyl group can be prepared by reacting the above-obtained compound (1-13) of the invention with carbon disulfide and alkylating the obtained dithioate.

The compound (1-9) of the invention can be reduced properly utilizing conventional methods available in the art, as by a procedure of reducing the compound (1-9) of the invention with hydrogen in an inert solvent in the presence of platinum oxide or like catalyst.

The reaction for producing the compound (1-14) from the compound (1-13) can be carried out by conventional methods, e.g. the method described in Bull. Chem. Soc. Jpn., 61, 285 (1988). Stated more specifically, the compound (1-14) can be prepared by reacting the compound (1-13) with carbon disulfide in the presence of a basic catalyst such as pyridine, followed by alkylation with alkyl halide.

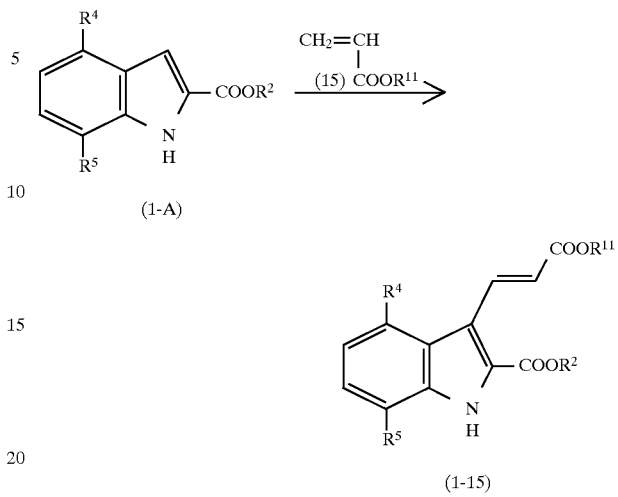

wherein $R^2$, $R^4$ and $R^5$ are as defined above, and $R^{11}$ is a $C_{1-4}$alkyl group.

According to Reaction Scheme-8, the compound (1-15) of the invention wherein $R^3$ is a 2-($C_{1-4}$alkoxy-carbonyl)vinyl group can be prepared by reacting the compound (1-A) of the invention with α,β-unsaturated ester of the formula (15). The reaction between the compound (1-A) of the invention and the compound of the formula (15) can be performed by conventional methods available in the art such as the method as disclosed in J. Org. Chem., 49, 2657 (1984), as in an inert solvent such as acetonitrile in the presence of palladium acetate or like catalyst.

The compound of the invention wherein $R^3$ is a 2-($C_{1-4}$alkoxycarbonyl)ethyl group can be prepared by reducing the compound (1-15) of the invention obtained above in Reaction Scheme-8. For example, a catalytic reduction may be conducted in an inert solvent such as ethanol, ethyl acetate or the like in the presence of platinum oxide or the like.

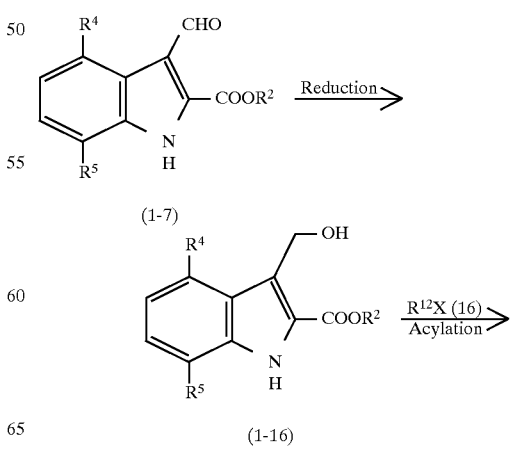

-continued
Reaction Scheme-9

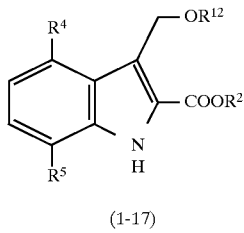

(1-17)

wherein $R^2$, $R^4$ and $R^5$ are as defined above, $R^{12}$ is a $C_{1-4}$acyl group and X is a halogen atom.

According to Reaction Scheme-9, the compound (1-16) of the invention wherein $R^3$ is a hydroxymethyl group can be prepared by reducing the compound (1-7) of the invention obtained above in Reaction Scheme-5. The compound (1-17) of the invention wherein $R^3$ is a ($C_{1-4}$acyloxy)methyl group can be prepared by acylating the above-obtained compound (1-16) of the invention.

The reduction of the compound (1-7) can be performed properly utilizing conventional methods available in the art as by a reaction of the compound (1-7) with sodium borohydride in methanol.

The compound (1-16) can be acylated properly utilizing conventional methods available in the art as by a reaction of the compound (1-16) with a halide of the formula (16) in a basic solvent such as pyridine.

The reaction between the compound (1-A) of the invention and the compound of the formula (17) can be performed by conventional methods available in the art, e.g. the method described in Synthesis, 1978, 374 as by a a procedure of reacting the compound (1-A) of the invention with the compound of the formula (17) in acetonitrile.

The compound of the formula (18) can be hydrolyzed by conventional methods available in the art, e.g. the method described in Synthesis, 1978, 374 as in acetone using an aqueous solution of potassium hydroxide.

According to Reaction Scheme-10, the compound (1-19) of the invention wherein $R^3$ is a halogen atom can be prepared by halogenating the compound (1-A) of the invention.

The compound (1-A) of the invention can be halogenated properly utilizing conventional methods available in the art such as the method stated in Heterocycles, 34, 2349 (1992), as by a reaction of the compound (1-A) of the invention with N-halosuccinimide in N,N-dimethylformamide.

According to Reaction Scheme-10, the compound (1-20) of the invention wherein $R^3$ is a $C_{1-4}$acyl group can be prepared by reacting the compound (1-A) of the invention with an acid anhydride of the formula (19) or with a carboxylic acid of the formula (20).

The reaction between the compound (1-A) of the invention and the compound of the formula (19) can be performed in 1,2-dichloroethane in the presence of Lewis acid such as anhydrous aluminum chloride according to the method described in Chem. Pharm. Bull., 38, 3261 (1990).

The reaction between the compound (1-A) of the invention and the compound of the formula (20) can be performed Reaction Scheme-10

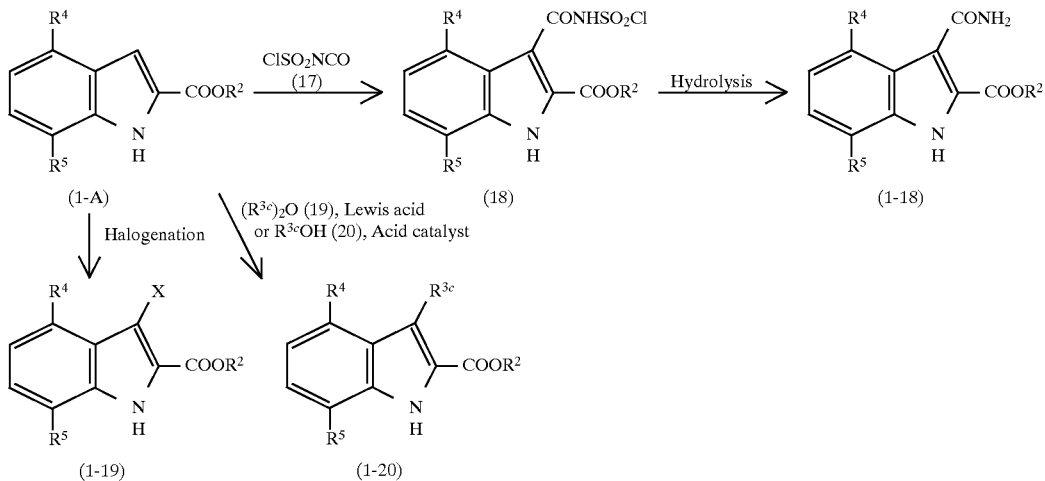

wherein $R^2$, $R^4$, $R^5$ and X are as defined above, and $R^{3c}$ is a $C_{1-4}$acyl group.

According to Reaction Scheme-10, the compound (1-18) of the invention wherein $R^3$ is a carbamoyl group can be prepared by reacting the compound (1-A) of the invention with a chlorosulfonyl isocyanate of the formula (17) to give a 3-(chlorosulfonyl)carbamoyl derivative of the formula (18), followed by hydrolysis of the derivative.

by conventional methods, as in acetonitrile in the presence of an acid catalyst such as anhydrous trifluoroacetic acid, polyphosphoric acid or the like according to the method disclosed in Chem. Pharm. Bull., 33, 4707 (1985).

Reaction Scheme-11

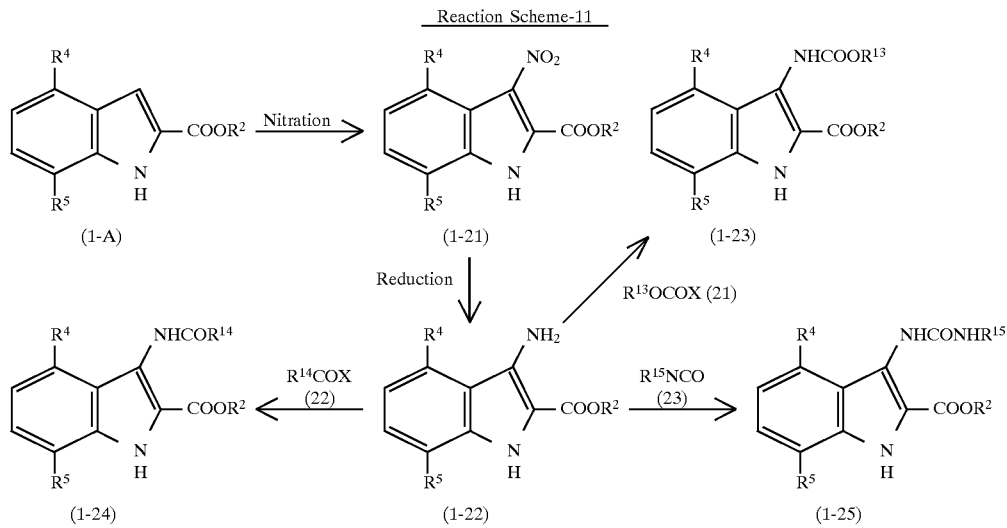

wherein $R^2$, $R^4$, $R^5$ and X are as defined above, $R^{13}$ is a $C_{1-4}$alkyl group, and $R^{14}$ and $R^{15}$ are $C_{1-4}$alkyl groups.

According to Reaction Scheme-11, the compound (1-21) of the invention wherein $R^3$ is a nitro group can be prepared by nitrating the compound (1-A) of the invention, and the compound (1-22) of the invention wherein $R^3$ is an amino group can be prepared by reducing the obtained compound (1-21) of the invention. The compound (1-23) of the invention wherein $R^3$ is a $C_{1-4}$alkoxycarbonylamino group can be prepared by reacting the compound (1-22) of the invention with a halogeno-formic acid ester of the formula (21). The compound (1-24) of the invention wherein $R^3$ is a $C_{1-4}$acylamino group can be prepared by reacting the compound (1-22) of the invention with an acyl halide of the formula (22). The compound (1-25) of the invention wherein $R^3$ is a 3-($C_{1-4}$alkyl)ureido group can be prepared by reacting the compound (1-22) of the invention with an isocyanate of the formula (23).

The compound (A-1) of the invention can be nitrated by a wide variety of conventional nitrating methods available in the art, for example, by a reaction of the compound (1-A) of the invention with a nitrating agent such as fuming nitric acid in an inert solvent such as chloroform or without a solvent.

The compound (1-21) can be reduced by a wide variety of methods known in the art for reducing a nitro group to an amino group, e.g. by a procedure of reducing a nitro group to an amino group in the presence of iron or tin in a mineral acid such as hydrochloric acid or an organic acid such as acetic acid. Also available is a method comprising reduction of the compound with hydrogen in an inert solvent such as ethanol in the presence of a catalytic reducing catalyst such as palladium on activated carbon, platinum oxide, platinum on activated carbon or palladium chloride.

The reaction of the compound (1-22) with the compound of the formula (21) can be made by conventional methods as in an inert solvent such as methylene chloride or without a solvent in the presence of an acid binder such as pyridine or triethylamine.

The reaction of the compound (1-22) with the compound of the formula (22) can be made by conventional methods as in an inert solvent such as methylene chloride or without a solvent in the presence of an acid binder such as pyridine or triethylamine.

The reaction of the compound (1-22) with the compound of the formula (23) can be made by conventional methods as in an inert solvent such as toluene or tetrahydrofuran or without a solvent.

Reaction Scheme-12

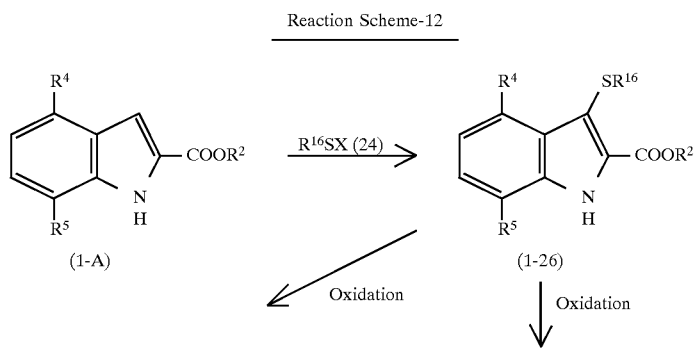

-continued
Reaction Scheme-12

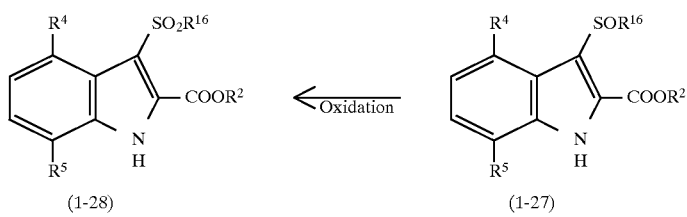

wherein $R^2$, $R^4$, $R^5$ and X are as defined above, and $R^{16}$ is a ($C_{1-4}$alkyl group or a phenyl group.

According to Reaction Scheme-12, the compound (1-26) of the invention wherein $R^3$ is a ($C_{1-4}$alkylsulfenyl group or a phenylsulfenyl group can be prepared by reacting the compound (1-A) of the invention with a sulfenyl halide of the formula (24). The compound (1-27) of the invention wherein $R^3$ is a $C_{1-4}$alkylsulfinyl group or a phenylsulfinyl group can be prepared by oxidizing the obtained compound (1-26) of the invention. Further, the compound (1-28) of the invention wherein $R^3$ is a $C_{1-4}$alkylsulfonyl group or a phenylsulfonyl group can be prepared by oxidizing the obtained compound (1-27) of the invention. The compound of (1-28) of the invention can be also prepared by oxidizing the compound (1-26) of the invention.

The reaction between the compound (1-A) of the invention and the compound of the formula (24) is conducted by conventional methods, as in an inert solvent such as 1,2-dichloroethane according to the method set out in J. Org. Chem., 59, 6372 (1994).

The compound (1-26) can be oxidized by treatment with an oxidizing agent in an inert solvent according to conventional methods described, e.g. in J. Med. Chem., 36, 1291 (1993). Examples of useful inert solvents are carbon tetrachloride, chloroform, 1,2-dichloroethane and like halogenated hydrocarbons, benzene, toluene and like aromatic hydrocarbons, diethyl ether, tetrahydrofuran, 1,4-dioxane and like ethers, acetone and like ketones, dimethylformamide, hexamethylphosphoric triamide (HMPA) and like amides, and dimethylsulfoxide and mixtures thereof. These solvents can be used in mixture with water. Useful oxidizing agents include, for example, peracetic acid, m-chloroperbenzoic acid and like organic peroxides, hydrogen peroxide and like inorganic peroxides, etc. A preferred amount of the oxidizing agent used is equimolar or substantially equimolar relative to the compound (1-26). The reaction temperature is not specifically limited but usually from −30° C. to the boiling point of the solvent to be used. The reaction time is variable with the amount of the oxidizing agent used, the reaction temperature, etc. but is usually 0.1 to 24 hours.

The oxidation of the compound (1-27) can be conducted in the same manner as done for the compound (1-26). The compound (1-28) can be produced from the compound (1-26) at once by properly adjusting the amount of the oxidizing agent to be used, the reaction temperature, the reaction time and other oxidizing reaction conditions.

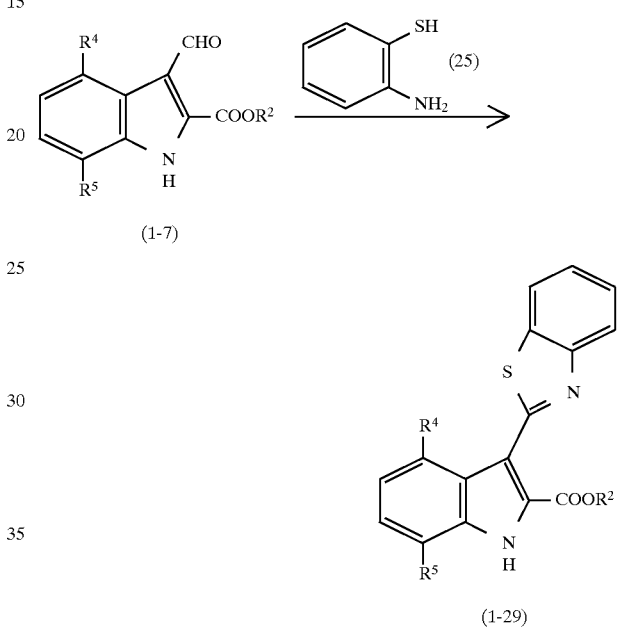

wherein $R^2$, $R^4$ and $R^5$ are as defined above.

According to Reaction Scheme-13, the compound (1-29) of the invention wherein $R^3$ is a benzothiazol-2-yl group can be prepared by reacting the compound (1-7) of the invention obtained above in Reaction Scheme-5 with a mercaptoamine of the formula (25).

The reaction between the compound (1-7) and the compound of the formula (25) can be conducted by conventional methods, e.g. in a solvent such as acetic acid according to the method disclosed in Tetrahedron Lett., 1984, 5327.

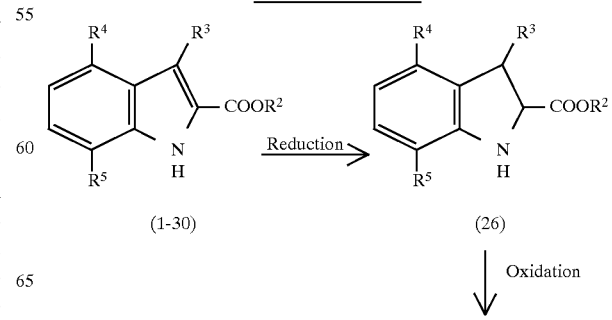

-continued
Reaction Scheme-14

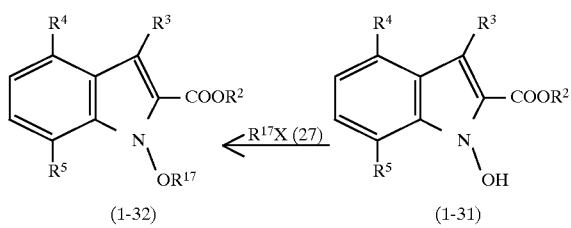

wherein $R^2$, $R^4$ and $R^5$ are as defined above, and $R^{17}$ is a $C_{1-4}$alkoxycarbonyl group, a $C_{1-4}$alkyl group or a $C_{1-4}$acyl group.

According to Reaction Scheme-14, the compound (1-31) of the invention wherein $R^1$ is a hydroxy group can be prepared by reducing the compound (1-30) of the invention prepared in the above respective reaction schemes to give an indoline-2-carboxylic acid ester of the formula (26), and oxidizing the compound of the formula (26). The compound (1-32) of the invention wherein $R^1$ is a $C_{1-4}$acyloxy group, a $C_{1-4}$alkoxy group or a ($C_{1-4}$alkoxycarbonyl)oxy group can be prepared by reacting the above-obtained compound (1-31) of the invention with a halide of the formula (27).

The compound (1-30) of the invention can be reduced by conventional methods, e.g. by a reaction of the compound (1-30) of the invention with magnesium in an inert solvent such as methanol. The compound of the formula (26) can be suitably oxidized by conventional methods, e.g. using sodium tungstate and hydrogen peroxide in an inert solvent such as methanol. These reducing and oxidizing methods are set forth in J. Med. Chem., 31, 944 (1988).

The reaction of the compound (1-31) with the compound of the formula (27) can be made in an inert solvent such as acetonitrile in the presence of an acid binder such as sodium hydroxide, potassium carbonate or the like. Examples of the compound of the formula (27) are alkyl halide, dialkyl sulfate, acyl halide, acid anhydride, etc.

Reaction Scheme-15

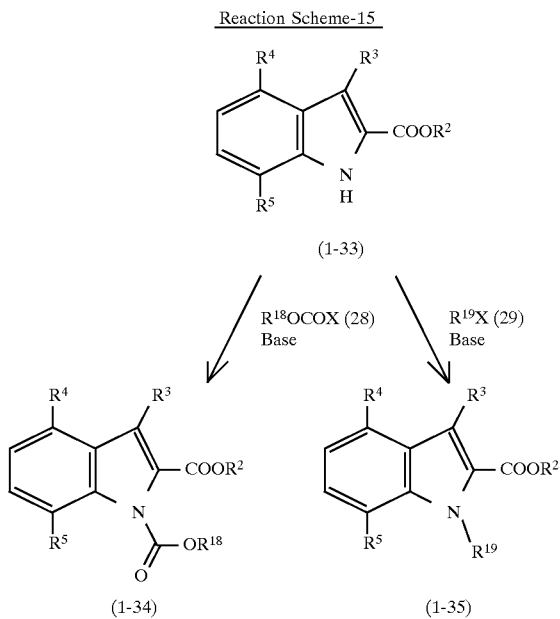

wherein $R^2$, $R^3$, $R^4$, $R^5$ and X are as defined above, $R^{18}$ is a $C_{1-4}$alkyl group or a phenyl group, and $R^{19}$ is a $C_{1-4}$acyl group.

According to Reaction Scheme-15, the compound (1-34) of the invention wherein $R^1$ is a phenoxycarbonyl group or a $C_{1-4}$alkoxycarbonyl group can be prepared by reacting the compound (1-33) of the invention with a halogeno-formic acid ester of the formula (28). The compound (1-35) of the invention wherein $R^1$ is a $C_{1-4}$acyl group can be prepared by reacting the compound (1-33) of the invention with an acyl halide of the formula (29).

The reaction of the compound (1-33) with the compound of the formula (28) can be made according to conventional methods available in the art, e.g. in an inert solvent such as N,N-dimethylformamide in the presence of a base such as sodium hydride.

The reaction of the compound (1-33) with the compound of the formula (29) can be made according to conventional methods available in the art, e.g. in an inert solvent such as N,N-dimethylformamide in the presence of a base such as sodium hydride.

The compounds (1) of the invention prepared by the above-mentioned processes can be easily isolated and purified from the reaction mixture by conventional separation methods such as solvent extraction, recrystallization or column chromatography. Consequently the compounds of the invention can be prepared by the foregoing processes with high purity and in a high yield.

In use as an active component of a fungicidal composition, the compound of the invention can be used as such without addition of other components. Usually the compound of the invention is mixed with a solid carrier, a liquid carrier, a gas carrier, a bait or the like and optionally with a surfactant or other adjuvants for the formulation of a fungicidal preparation, and the mixture is formulated into an oil solution, emulsifiable concentrate, wettable powder, suspension concentrate, granules, dust, aerosol, fumigant or the like.

Examples of solid carriers to be used in the formulation of a fungicidal preparation are fine particles, granules or otherwise formulated preparations of clay (such as kaolin clay, diatomaceous earth, synthetic hydrous silicon oxide, bentonite, Fubasami clay and acid clay), talc, ceramics, other inorganic minerals (such as Celite, quartz, sulfur, active carbon, calcium carbonate and hydrated silica), chemical manure (such as ammonium sulfate, ammonium phosphate, ammonium nitrate, urea and ammonium chloride) or the like. Examples of useful liquid carriers are water, alcohols (such as methanol and ethanol), ketones (such as acetone and methyl ethyl ketone), aromatic hydrocarbons (such as benzene, toluene, xylene, ethylbenzene and methylnaphthalene), aliphatic hydrocarbons (such as hexane, cyclohexane, kerosene and light oil), esters (such as ethyl acetate and butyl acetate), nitriles (such as acetonitrile and isobutyronitrile), ethers (such as diisopropyl ether and dioxane), acid amides (such as N,N-dimethylformamide and N,N-dimethylacetamide), halogenated hydrocarbons (such as dichloromethane, trichloroethane and carbon tetrachloride), dimethylsulfoxide, and vegetable oils (such as soybean oil and cotton-seed oil), etc. Examples of useful gas carriers, i.e. propellants are flon gas, butane gas, LPG (liquefied petroleum oil), dimethyl ether, carbon dioxide gas, etc.

Examples of useful surfactants are alkylsulfates, alkylsulfonates, alkylaryl sulfonates, alkylaryl ethers, polyoxyethylene compounds, polyethylene glycol ethers, polyhydric alcohol esters, suguar-alcohol derivatives, etc.

Examples of useful aids for formulation such as binders and dispersants are casein, gelatin, polysaccharides (such as starch powder, gum arabic, cellulose derivatives and alginic acid), lignin derivatives, bentonite, saccharides, synthetic water-soluble high molecular weight substances (such as polyviyl alcohol, polyvinyl pyrrolidone and polyacrylic acids), etc. Examples of useful stabilizers are PAP (acid isopropyl phosphate), BHT (2,6-di-tert-butyl-4-methylphenol), BHA (mixture of 2-tert-butyl-4-methoxyphenol and 3-tert-butyl-4-methoxyphenol), vegetable oils, mineral oils, surfactants and aliphatic acids, and esters thereof.

The fungicidal preparation thus obtained is used as such or as diluted with water or the like. When required, the fungicidal preparation can be used as mixed with, or simultaneously with (without being mixed together) other fungicides, insecticides, nematocides, miticides, herbicides, plant-growth regulators, synergists, soil improvers, baits, etc.

Since the compounds of the invention show selectively high fungicidal activity against fungicide-resistant fungi, the compounds are suitable for use when there exist fungicide-resistant fungi. If fungicide-sensitive fungi co-exist with fungicide-resistant fungi, the compound of the invention may be used in mixture with conventional benzimidazole.thiophanate fungicides or may be alternately used.

For use as an agricultural or horticultural fungicide, the compound of the invention is applied usually in an amount of 10 to 100 g per 10 res. When an emulsifiable concentrate, wettable powder, suspension concentrate or the like is used as diluted with water, the concentration of the compound to be applied is usually 10 to 5,000 ppm. It is desirable to use a granular or powder preparation as it is, without dilution.

The amount and concentration of the compound to be applied are variable with the kind of the fungicidal preparation, time of application, application site, application method, type of the disease to be controlled, kind of crops, the degree of damage, etc. and can be increased or reduced without limitation to said range.

BEST MODE FOR CARRYING OUT THE INVENTION

The present invention will be more easily understood from the following preparation examples, formulation examples and test examples of compounds of the invention. These examples are not limitative but illustrative. In the examples, parts are by weight unless otherwise specified.

PREPARATION EXAMPLE 1

Synthesis of methyl 7-chloro-4-methylindole-2-carboxylate (compound 1)

(a) A solution of 4.0 g (25.6 mmol) of 2-chloro-5-methylphenylhydrazine in 300 ml of benzene was prepared. Thereto were added 3.0 g (128 mmol) of methyl pyruvate and one drop (by a pipette) of boron trifluoride-diethyl etherate. The reaction mixture was refluxed for 2 hours. After distilling off benzene, the residue was purified by silica gel chromatography (hexane:ethyl acetate=10:1) to provide 6.15 g of methyl pyruvate 2-chloro-5-methylphenylhydrazone (100%).

(b) To 3.5 g (14.5 mmol) of the above-obtained methyl pyruvate 2-chloro-5-methylphenylhydrazone was added 7.0 g of polyphosphoric acid. The reaction mixture was stirred at 180° C. for 30 minutes. While the reaction mixture was cooled, 30 ml of water was added. The reaction mixture was extracted with ether. The extract was washed with 5% aqueous sodium hydrogencarbonate solution and saturated aqueous sodium chloride solution and dried over magnesium sulfate. After distilling off the solvent, the residue was purified by silica gel chromatography (hexane:ethyl acetate= 4:1) to provide 2.01 g of the title compound (62%).

m.p.: 133°–134° C.; $^1$H-NMR (90 MHz, CDCl$_3$/TMS; δppm): 2.53 (s, 3H), 3.97 (s, 3H), 6.87 (d, 1H), 7.21 (d, 1H), 7.28 (d, 1H), 9.02 (brs, 1H)

PREPARATION EXAMPLE 2

Synthesis of methyl 4,7-dimethoxyindole-2-carboxylate (compound 2)

(a) While 23 ml of sodium methoxide (28% solution in methanol) in 40 ml of anhydrous methanol was stirred vigorously, 40 ml of a mixed methanol solution containing 4.0 g (21.1 mmol) of 2,5-dimethoxybenzaldehyde and 9.7 g (84.2 mmol) of methyl azidoacetate was added dropwise at −15° C. After completion of the addition, the reaction mixture was stirred for 2 hours. Then the reaction mixture was poured into a saturated ammonium chloride solution and extracted with ethyl acetate. The extract was washed with water and dried over magnesium sulfate. After distilling off the solvent, the residue was purified by silica gel chromatography (hexane:ethyl acetate=10:1) to provide 3.1 g of methyl 2,5-dimethoxyphenyl-α-azidocinnamate.

(b) A solution of 1.5 g (6.84 mmol) of the above-obtained methyl 2,5-dimethoxyphenyl-α-azidocinnamate in 300 ml of xylene was refluxed for 4 hours. After distilling off xylene, the residue was recrystallized from methanol to provide 1.01 g of the title compound (74.7%).

m.p.: 145°–146° C.; $^1$H-NMR (90 MHz, CDCl$_3$/TMS; δppm): 3.91 (s, 3H), 3.92 (s, 6H), 6.35 (d, 1H), 6.60 (d, 1H), 7.30 (d, 1H), 9.02 (brs, 1H)

PREPARATION EXAMPLES 3–28

The following compounds of the invention were prepared in the same manner as in Preparation Examples 1 and 2.

Methyl 4,7-dichloroindole-2-carboxylate (compound 3)
m.p.: 157°–158° C.; $^1$H-NMR (90 MHz, CDCl$_3$/TMS; δppm): 3.98 (s, 3H), 7.09 (d, 1H), 7.25 (d, 1H), 7.33 (d, 1H), 9.08(brs, 1H)

Methyl 4-chloro-7-methylindole-2-carboxylate (compound 4)
m.p.: 162°–163° C.; $^1$H-NMR (90 MHz, CDCl$_3$/TMS; δppm): 2.49 (s, 3H), 3.96 (s, 3H), 7.05 (s, 2H), 7.32 (d, 1H), 8.95 (brs, 1H)

Methyl 4-chloro-7-methoxyindole-2-carboxylate (compound 5)
m.p.: 146°–147° C.; $^1$H-NMR (90 MHz, CDCl$_3$/TMS; δppm): 3.95 (s, 6H), 6.61 (d, 1H), 7.01 (d, 1H), 7.27 (d, 1H), 9.14 (brs, 1H)

Methyl 4,7-dimethylindole-2-carboxylate (compound 6)
m.p.: 145°–146° C.; $^1$H-NMR (90 MHz, CDCl$_3$/TMS; δppm): 2.48 (s, 3H), 2.53 (s, 3H), 3.95 (s, 3H), 6.85 (d, 1H), 7.02 (d, 1H), 7.27 (d, 1H), 8.77 (brs, 1H)

Methyl 7-methoxy-4-methylindole-2-carboxylate (compound 7)
m.p.: 119°–120° C.; $^1$H-NMR (90 MHz, CDCl$_3$/TMS; δppm): 2.47 (s, 3H), 3.93 (s, 6H), 6.60 (d, 1H), 6.81 (d, 1H), 7.24 (d, 1H), 9.07 (brs, 1H)

Methyl 4-methoxy-7-methylindole-2-carboxylate (compound 8)
m.p.: 142°–143° C.; $^1$H-NMR (90 MHz, CDCl$_3$/TMS; δppm): 2.43 (s, 3H), 3.93 (s, 6H), 6.42 (d, 1H), 7.00 (d, 1H), 7.34 (d, 1H), 8.82 (brs, 1H)

Methyl 7-chloro-4-methoxyindole-2-carboxylate (compound 9)
m.p.: 137°–138° C.; $^1$H-NMR (90 MHz, CDCl$_3$/TMS; δppm): 3.95 (s, 6H), 6.44 (d, 1H), 7.21 (d, 1H), 7.34 (d, 1H), 8.96 (brs, 1H)

Methyl 7-methyl-4-nitroindole-2-carboxylate (compound 10)

m.p.: 249°–250° C.; ¹H-NMR (90 MHz, CDCl₃/TMS; δppm): 2.69 (sr 3H), 3.98 (s, 3H), 7.17 (d, 1H), 7.73 (d, 1H), 8.04 (d, 1H), 11.6 (brs, 1H)

Methyl 4-bromo-7-methylindole-2-carboxylate (compound 11)

m.p.: 165°–166° C.; ¹H-NMR (90 MHz, CDCl₃/TMS; δppm): 2.48 (s, 3H), 3.97 (s, 3H), 6.97 (d, 1H), 7.23 (d, 1H), 7.29 (d, 1H), 8.92 (brs, 1H)

Methyl 4-iodo-7-methylindole-2-carboxylate (compound 12)

m.p.: 177°–178° C.; ¹H-NMR (90 MHz, CDCl₃/TMS; δppm): 2.53 (s, 3H), 3.95 (s, 3H), 6.81 (d, 1H), 7.07 (d, 1H), 7.41 (d, 1H), 11.0 (brs, 1H)

Methyl 4-chloro-7-ethylindole-2-carboxylate (compound 13)

m.p.: 152°–153° C.; ¹H-NMR (90 MHz, CDCl₃/TMS; δppm): 1.32 (t, 3H), 2.93 (q, 2H), 3.95 (s, 3H), 7.05 (s, 2H), 7.27 (d, 1H), 10.5 (brs, 1H)

Methyl 4-chloro-7-isopropylindole-2-carboxylate (compound 14)

m.p.: 147°–148° C.; ¹H-NMR (90 MHz, CDCl₃/TMS; δppm): 1.36 (d, 6H), 3.23 (m, 1H), 3.97 (s, 3H), 7.11 (s, 2H), 7.33 (d, 1H), 8.95 (brs, 1H)

Methyl 7-bromo-4-chloroindole-2-carboxylate (compound 15)

m.p.: 147°–148° C.; ¹H-NMR (90 MHz, CDCl₃/TMS; δppm): 3.98 (s, 3H), 7.06 (d, 1H), 7.38 (d, 1H), 7.40 (d, 1H), 9.05 (brs, 1H)

Methyl 4-ethoxy-7-methylindole-2-carboxylate (compound 16)

m.p.: 167°–168° C.; ¹H-NMR (90 MHz, CDCl₃/TMS; δppm): 1.47 (t, 3H), 2.43 (s, 3H), 3.93 (s, 3H), 4.07 (q, 2H), 6.40 (d, 1H), 6.98 (d, 1H), 7.37 (d, 1H), 8.90 (brs, 1H)

Methyl 7-methyl-4-propoxyindole-2-carboxylate (compound 17)

m.p.: 128°–129° C.; ¹H-NMR (90 MHz, CDCl₃/TMS; δppm): 1.03 (t, 3H), 1.80 (m, 2H), 2.44 (s, 3H), 3.93 (s, 3H), 4.30 (t, 2H), 6.41 (d, 1H), 7.00 (d, 1H), 7.35 (d, 1H), 8.90 (brs, 1H)

Methyl 4-isopropyl-7-methylindole-2-carboxylate (compound 18)

m.p.: 157°–158° C.; ¹H-NMR (90 MHz, CDCl₃/TMS; δppm): 1.38 (d, 6H), 2.43 (s, 3H), 3.92 (s, 3H), 5.27 (m, 1H), 6.41 (d, 1H), 7.00 (d, 1H), 7.33 (d, 1H), 8.90 (brs, 1H)

Methyl 4-allyloxy-7-methylindole-2-carboxylate (compound 19)

m.p.: 145°–147° C.; ¹H-NMR (90 MHz, CDCl₃/TMS; δppm): 2.43 (s, 3H), 3.93 (s, 3H), 4.85 (d, 2H), 5.2–5.5 (m, 2H), 5.9–6.3 (m, 1H), 6.42 (d, 1H), 7.01 (d, 1H), 7.39 (d, 1H), 8.90 (brs, 1H)

Methyl 7-methyl-4-(2-propynyloxy)indole-2-carboxylate (compound 20)

m.p.: 160°–162° C.; ¹H-NMR (90 MHz, CDCl₃/TMS; δppm): 2.43 (s, 3H), 2.53 (t, 1H), 3.92 (s, 3H), 4.94 (d, 2H), 6.42 (d, 1H), 7.02 (d, 1H), 7.43 (d, 1H), 8.90 (brs, 1H)

Methyl 4-benzyloxy-7-methylindole-2-carboxylate (compound 21)

m.p.: 172°–173° C.; ¹H-NMR (90 MHz, CDCl₃/TMS; δppm): 2.42 (s, 3H), 3.91 (s, 3H), 5.38 (s, 2H), 6.41 (d, 1H), 7.00 (d, 1H), 7.3–7.5 (m, 6H), 8.90 (brs, 1H)

Methyl 7-methyl-4-methylsulfenylindole-2-carboxylate (compound 22)

m.p.: 144°–145° C.; ¹H-NMR (90 MHz, CDCl₃/TMS; δppm): 2.48 (s, 3H), 2.54 (s, 3H), 3.95 (s, 2H), 6.93 (d, 1H), 7.07 (d, 1H), 7.35 (d, 1H), 9.00 (brs, 1H)

Methyl 7-methyl-4-methylsulfonylindole-2-carboxylate (compound 23)

m.p.: 212°–213° C.; ¹H-NMR (90 MHz, CDCl₃/TMS; δppm): 2.63 (s, 3H), 3.12 (s, 3H), 3.99 (s, 3H), 7.26 (d, 1H), 7.66 (d, 1H), 7.75 (d, 1H), 9.40 (brs, 1H)

Methyl 4-chloro-7-propylindole-2-carboxylate (compound 24)

m.p.: 124°–125° C.; ¹H-NMR (90 MHz, CDCl₃/TMS; δppm): 0.91 (t, 3H), 1.70 (m, 2H), 2.72 (t, 2H), 3.90 (s, 3H), 6.95 (s, 2H), 7.25 (d, 1H), 9.00 (brs, 1H)

Methyl 7-benzyl-4-chloroindole-2-carboxylate (compound 25)

m.p.: 145°–146° C.; ¹H-NMR (90 MHz, CDCl₃/TMS; δppm): 3.91 (s, 3H), 4.20 (s, 2H), 7.05 (d, 1H), 7.12 (d, 1H), 7.27 (m, 5H), 7.30 (d, 1H), 8.85 (brs, 1H)

Methyl 4-chloro-7-phenylindole-2-carboxylate (compound 26)

m.p.: 141°–142° C.; ¹H-NMR (90 MHz, CDCl₃/TMS; δppm): 3.89 (s, 2H), 7.20 (s, 2H), 7.35 (d, 1H), 7.49 (m, 5H), 9.10 (brs, 1H)

Ethyl 4,7-dichloroindole-2-carboxylate (compound 27)

m.p.: 129°–130° C.; ¹H-NMR (90 MHz, CDCl₃/TMS; δppm): 1.43 (t, 3H), 4.41 (q, 2H), 7.04 (d, 1H), 7.25 (d, 1H), 7.33 (d, 1H), 9.06 (brs, 1H)

Isopropyl 4,7-dichloroindole-2-carboxylate (compound 28)

m.p.: 122°–123° C.; ¹H-NMR (90 MHz, CDCl₃/TMS; δppm): 1.34 (d, 6H), 5.31 (m, 1H), 7.10 (d, 1H), 7.26 (d, 1H), 7.32 (d, 1H), 9.11 (brs, 1H)

PREPARATION EXAMPLE 29

Synthesis of ethyl 4-chloro-3,7-dimethylindole-2-carboxylate (compound 29)

1) Synthesis of ethyl 2-N-5'-chloro-2'-methylphenylhydrazonobutyrate (intermediate compound)

While 6.00 g (42.4 mmol) of 5-chloro-2-methylaniline was cooled in a ice-salt bath, 14 ml of concentrated hydrochloric acid was added such that the temperature of the reaction mixture did not exceed 5° C. Then 12 ml of an aqueous solution of 3.22 g (46.6 mmol) of sodium nitrite was added such that the temperature of the reaction mixture did not exceed 5° C. Thus an aqueous solution of diazonium salt was synthesized. On the other hand, 7.37 g (46.6 mmol) of ethyl 2-ethylacetoacetate was dissolved in 20 ml of ethanol and cooled with ice-methanol and then 16.2 g of a 50% potassium hydroxide aqueous solution was added. The above aqueous solution of diazonium salt was added thereto dropwise over a period of 20 minutes and the reaction mixture was stirred for 30 minutes. The reaction mixture was filtered and extracted with ethyl acetate. The extract was washed with water, dried over magnesium sulfate and concentrated. The crude product was purified by silica gel column chromatography (ethyl acetate:n-hexane=1:20) to provide 5.49 g of ethyl 2-N-5'-chloro-2'-methylphenylhydrazonobutyrate as orange crystals. Yield: 48%

¹H-NMR (300 MHz, CDCl₃/TMS; δppm): 7.68 (s, 1H), 7.58 (d, 1H), 6.85 (dd, 1H), 4.33 (q, 2H), 2.62 (q, 2H), 2.14 (s, 3H), 1.39 (t, 3H), 1.17 (t, 3H)

2) Synthesis of ethyl 4-chloro-3,7-dimethylindole-2-carboxylate (compound 29)

A reactor was charged with 5.00 g of ethyl 2-N-5'-chloro-2'-methylphenylhydrazonobutyrate and 10.5 g of polyphosphoric acid. The reaction mixture was stirred and heated to 180° C. The reaction mixture was stirred for 1 hour and then cooled to 60° C. and 50 ml of water was added. The reaction mixture was extracted with 40 ml of ethyl acetate three times. The extract was washed with aqueous sodium hydrogencarbonate solution and saturated aqueous sodium chloride solution, dried over magnesium sulfate and concentrated. The crude crystals were recrystallized from methanol to provide 1.80 g of beige crystals. Yield: 38% m.p.: 118°–119° C.; $^1$H-NMR (300 MHz, CDCl$_3$/TMS; δppm): 8.6 (brs, 1H), 6.97 (s, 2H), 4.43 (q, 2H), 2.88 (s, 3H), 2.49 (s, 3H), 1.44 (t, 3H)

PREPARATION EXAMPLE 30

Synthesis of methyl 4-chloro-3,7-dimethylindole-2-carboxylate (compound 30)

1) Synthesis of 4-chloro-3,7-dimethylindole-2-carboxylic acid (intermediate compound)

In 20 ml of ethanol and 5 ml of water were dissolved 1.50 g (6.0 mmol) of ethyl 4-chloro-7-methylindole-2-carboxylate and 0.5 g (9.0 mmol) of potassium hydroxide. The reaction mixture was refluxed for 4 hours. The solution was concentrated and then 1N HCl aqueous solution was added. The precipitates were separated by filtration, dissolved in 50 ml of diethyl ether and extracted with 30 ml of aqueous sodium hydrogencarbonate solution three times. The extract was washed with 30 ml of diethyl ether. The water layers were made acid with 1N HCl aqueous solution and extracted with 30 ml of diethyl ether three times. The extract was dried over anhydrous magnesium sulfate and concentrated to provide 0.91 g of beige crystals. Yield: 68% m.p.: 211°–213° C.; $^1$H-NMR (300 MHz, CDCl$_3$/TMS; δppm): 8.66 (brs, 1H), 7.01 (m, 2H), 2.93 (s, 3H), 2.46 (s, 3H)

2) Synthesis of methyl 4-chloro-3,7-dimethylindole-2-carboxylate (compound 30)

An excess diazomethane ether solution was added to an ether solution of 0.50 g (2.24 mmol) of 4-chloro-3,7-dimethylindole-2-carboxylic acid under ice-cooling. The reaction mixture was allowed to stand for 30 minutes and then washed with 1N HCl aqueous solution and aqueous saturated sodium chloride solution. The ether layer was dried over anhydrous magnesium sulfate and concentrated under reduced pressure to provide white crystals. The crude crystals were purified by silica gel column chromatography to provide 0.41 g of white crystals. Yield: 77% m.p.: 122°–123° C.; $^1$H-NMR (300 MHz, CDCl$_3$/TMS; δppm): 8.62 (s, 1H), 6.99 (d, 1H), 6.97 (d, 1H), 3.97 (s, 3H), 2.88 (s, 3H), 2.44 (s, 3H)

PREPARATION EXAMPLE 31

Synthesis of ethyl 4,7-dichloro-3-methylindole-2-carboxylate (compound 31)

The title compound was prepared in the same manner as in Preparation Example 29. Yield: 24.5% m.p.: 107°–108° C.; $^1$H-NMR (300 MHz, CDCl$_3$/TMS; δppm): 8.85 (brs, 1H), 7.18 (d, 1H), 7.02 (d, 1H), 4.45 (q, 2H), 2.87 (s, 3H), 1.46 (t, 2H)

PREPARATION EXAMPLE 32

Synthesis of methyl 4,7-dichloro-3-methylindole-2-carboxylate (compound 32)

The title compound was prepared in the same manner as in Preparation Example 29. Yield: 15.0% m.p.: 110°–111° C.; $^1$H-NMR (300 MHz, CDCl$_3$/TMS; δppm): 8.85 (brs, 1H), 7.17 (d, 1H), 7.01 (d, 1H), 3.98 (s, 3H), 2.86 (s, 3H)

PREPARATION EXAMPLE 33

Synthesis of methyl 4-chloro-7-methyl-3-propylindole-2-carboxylate (compound 33)

While a solution of 6.00 g (42.4 mmol) of 5-chloro-2-methylaniline in 10 ml of ethanol was cooled in an ice-salt bath, 12 ml of concentrated hydrochloric acid was added such that the temperature of the reaction mixture did not exceed −5° C. Then a solution of 3.22 g (46.6 mmol) of sodium nitrite in 12 ml of water was added such that the temperature of the reaction mixture did not exceed −5° C. Thus an aqueous solution of diazonium salt was synthesized. On the other hand, 8.03 g (46.6 mmol) of methyl 2-butyl-acetoacetate was dissolved in 20 ml of ethanol and then cooled in an ice-salt bath. After addition of 12 g of ice, 16.2 g of 50% aqueous potassium hydroxide solution was added. Then the above-obtained aqueous diazonium salt solution was added dropwise over a period of 20 minutes and the reaction mixture was stirred for 30 minutes. The reaction mixture was filtered and extracted with ethyl acetate. The extract was washed with water, dried over magnesium sulfate and concentrated to provide 12.57 g of crude methyl 2-N-5'-chloro-2'-methylphenylhydrazono-hexanoate. After addition of 26 g of polyphosphoric acid, the reaction mixture was stirred. The reaction mixture was stirred and heated to 180° C. The reaction mixture was stirred for 5 minutes and cooled to 60° C., followed by addition of 50 ml of water. The reaction mixture was extracted with 100 ml of ethyl acetate 5 times. The extract was washed with aqueous sodium hydrogencarbonate solution and saturated aqueous sodium chloride solution, dried over magnesium sulfate and concentrated. The crude crystals were purified by silica gel column chromatography (ethyl acetate: n-hexane=1:9) and recrystallized from diethylether-n-hexane to provide 1.65 g of beige crystals.

Yield: 15% m.p.: 109°–110° C.; $^1$H-NMR (300 MHz, CDCl$_3$/TMS; δppm): 8.66 (brs, 1H), 7.02–6.92 (m, 2H), 3.96 (s, 3H), 3.4–3.3 (m, 2H), 2.44 (s, 3H), 1.75–1.66 (m, 2H), 1.01 (t, 3H)

PREPARATION EXAMPLE 34

Synthesis of methyl 3-allyl-4,7-dimethylindole-2-carboxylate (compound 34)

Under nitrogen atmosphere, 1.00 g (3.54 mmol) of methyl 3-bromo-4,7-dimethylindole-2-carboxylate and 0.31 g (5.23 mmol) of dichloro [1,1-bis(diphenylphos-phino)ferrocene] palladium (PdCl$_2$(dppf)) were suspended in 4 ml of anhydrous dimethylformamide (DMF). Thereto were added 0.57 ml (5.32 mmol) of allyl acetate and 2.7 ml (5.32 mmol) of hexabutylditin. The reaction mixture was stirred at 120° C. for 90 minutes and then subjected to Celite filtration. The filtrate was extracted with chloroform. The extract was purified by silica gel column chromatography (chloroform:n-hexane=1:1 to 3:1) to provide 0.75 g of white crystals. Yield: 87% m.p.: 135°–136° C.; $^1$H-NMR (300 MHz, CDCl$_3$/TMS; δppm): 8.61 (brs, 1H), 6.98 (d, 1H), 6.77 (d, 1H), 6.13–6.01 (m, 1H), 5.04–4.85 (m, 2H), 4.06–3.91 (m, 5H), 2.67 (s, 3H), 2.45 (s, 3H)

PREPARATION EXAMPLE 35

Synthesis of methyl 4,7-dimethyl-3-phenylindole-2-carboxylate (compound 35)

Under nitrogen atmosphere, 0.12 g (0.11 mmol) of tetrakis(triphenylphosphine)palladium (0) was suspended in 10 ml of anhydrous DMF. Thereto was added a solution of 1.00 g (3.54 mmol) of methyl 3-bromo-4,7-diemthylindole-2-carboxylate in 10 ml of anhydrous DMF. After the reaction mixture was stirred at room temperature for 10 minutes, a solution of 0.81 g (5.32 mmol) of phenyl borate in 6 ml of anhydrous methanol was added, followed by addition of 3.54 ml (7.09 mmol) of 2N sodium carbonate aqueous solution. The reaction mixture was refluxed for 15 hours and then extracted with chloroform. The extract was purified by silica gel column chromatography (chloroform: n-hexane= 1:1 to 1:0) to provide 0.60 g of white crystals. Yield: 60% m.p.: 143°–145° C.; $^1$H-NMR (300 MHz, CDCl$_3$/TMS; δppm): 8.80 (brs, 1H), 7.38 (s, 5H), 7.03 (d, 1H), 6.77 (d, 1H), 3.71 (s, 3H), 2.52 (s, 3H), 2.01 (s, 3H)

PREPARATION EXAMPLE 36

Synthesis of ethyl 4,7-dimethyl-3-phenylindole-2-carboxylate (compound 36)

The title compound was prepared in the same manner as in Preparation Example 35. The compound was obtained as white crystals. Yield: 34% m.p.: 107°–108° C.; $^1$H-NMR (300 MHz, CDCl$_3$/TMS; δppm): 8.81 (brs, 1H), 7.37 (s, 5H), 7.03 (d, 1H), 6.77 (d, 1H), 4.15 (q, 2H), 2.52 (s, 3H), 2.02 (s, 3H), 1.04 (t, 3H)

PREPARATION EXAMPLE 37

Synthesis of methyl 3-formyl-4,7-dimethylindole-2-carboxylate (compound 37)

A 500-ml 3-necked flask dried with heating was charged with 71 ml of anhydrous DMF. Then 21.5 ml (230 mmol) of phosphorus oxychloride was added dropwise at 0° C. over a period of 40 minutes and stirring was continued until the solution turned red. A solution of 50 g (246 mmol) of methyl 4,7-dimethylindole-2-carboxylate in 200 ml of anhydrous DMF was added dropwise at 20°–30° C. over a period of at least 30 minutes, and the reaction mixture was stirred at 90° C. for 2 hours. The reaction mixture was poured upon 500 g of ice and made basic by gradually adding 225 ml of aqueous solution of 40 g of sodium hydroxide. The solution thus obtained was refluxed for 1 minute and immediately filtered. The crystals precipitated were washed with 100 ml of water four times and dried under reduced pressure. The crude product was purified by silica gel column chromatography to provide 29.5 g of light yellow crystals. Yield: 26% m.p.: 174°–175° C.; $^1$H-NMR (300 MHz, DMSO/TMS; δppm): 10.78 (s, 1H), 9.21 (brs, 1H), 7.09 (d, 1H), 6.99 (d, 1H), 4.05 (s, 1H), 2.78 (s, 3H), 2.50 (s, 3H)

PREPARATION EXAMPLE 38

Synthesis of ethyl 4-chloro-3-methoxycarbonyl-7-methylindole-2-carboxylate (compound 38)

A solution of 180 mg (0.673 mmol) of 4-chloro-7-methyl-3-methoxycarbonylindole-2-carboxylic acid in 10 ml of ethanol was prepared and 1 ml of sulfuric acid was added. The reaction mixture was refluxed for 6 hours. After ethanol was distilled off under reduced pressure, the residue was poured into 50 ml of ice water and extracted with 15 ml of ethyl acetate three times. The ethyl acetate layers were collected, washed with 30 ml of water and 15 ml of 5% sodium hydrogencarbonate aqueous solution, dried over anhydrous magnesium sulfate and concentrated under reduced pressure, thus giving 0.20 g of white crystals. Yield: quantitative m.p.: 143°–144° C.; $^1$H-NMR (300 MHz, CDCl$_3$/TMS; δppm): 10.08 (brs, 1H), 7.07 (m, 2H), 4.44 (q, 2H), 4.03 (s, 3H), 2.53 (s, 3H), 1.43 (t, 3H)

PREPARATION EXAMPLE 39

Synthesis of methyl 4-chloro-3-methoxycarbonyl-7-methylindole-2-carboxylate (compound 39)

While 22.6 g (160 mmol) of 5-chloro-2-methylaniline was cooled with an ice-salt bath under nitrogen atmosphere, 300 ml of anhydrous methanol was added. Then 25 g (176 mmol) of dimethyl acetylene dicarboxylate was added over a period of 15 minutes and the reaction mixture was stirred for 30 minutes. Stirring was further continued at room temperature for 3 hours. The reaction mixture was concentrated and recrystallized from methanol to provide 39.8 g of dimethyl 2-N-5'-chloro-2'-methylphenylamino-cis-butenedioate (intermediate compound) as yellow crystals. Yield: 88%

Under nitrogen atmosphere, 19.0 g (66.8 mmol) of the above dimethyl 2-N-5'-chloro-2'-methylphenylamino-cis-butenedioate and 30.9 g (138 mmol) of palladium acetate were dissolved in 450 ml of anhydrous DMF and stirred at 80° C. for 3.5 hours. The reaction mixture was subjected to Celite filtration and the filtrate was concentrated. The residue was dissolved in ethyl acetate and subjected to Celite filtration again. The filtrate was concentrated and the residue was purified by silica gel column chromatography (ethyl acetate: n-hexane=1:2) and recrystallized from methanol, thus giving 11.5 g of white crystals. Yield: 59% m.p.: 173°–174° C.; $^1$H-NMR (300 MHz, CDCl$_3$/TMS; δppm): 9.01 (brs, 2H), 7.12–7.04 (m, 2H), 4.04 (s, 3H), 4.00 (s, 3H), 2.46 (s, 3H)

PREPARATION EXAMPLE 40

Synthesis of 4-chloro-2-methoxycarbonyl-7-methylindole-2-carboxylic acid (compound 40)

A mixture of 0.66 g (4.95 mmol) of anhydrous aluminum chloride and 10 ml of carbon disulfide was prepared. Thereto was added dropwise 0.63 g of oxalyl chloride over a period of 30 minutes while maintaining the temperature of the reaction mixture at 10°–15° C. The reaction mixture was stirred for 15 minutes and then 5 ml of a solution of 1.0 g (1.5 mmol) of methyl 4-chloro-7-methylindole-2-carboxylate in carbon disulfide was added dropwise over a period of 1 hour. The reaction mixture was refluxed with heating for 1 hour and then poured over a mixture of concentrated hydrochloric acid and ice. The reaction mixture was extracted with carbon tetrachloride. The carbon tetrachloride layer was washed with water and back-extracted with 10% sodium hydroxide aqueous solution. And then 6N HCl aqueous solution was added to 10% sodium hydroxide aqueous solution. The crystals precipitated were collected by filtration and dried to provide white powder.

Yield: 10% $^1$H-NMR (300 MHz, DMSO/TMS; δppm): 12.5 (brs, 1H), 9.00 (brs, 2H), 7.01–6.98 (m, 2H), 3.84 (s, 3H), 2.48 (s, 3H)

PREPARATION EXAMPLE 41

Synthesis of methyl 3-methoxycarbonyl-4,7-dimethylindole-2-carboxylate (compound 41)

The title compound was prepared in the same manner as in Preparation Example 39. The compound was obtained as yellow crystals. Yield: 52% m.p.: 143°–144° C.; $^1$H-NMR (300 MHz, CDCl$_3$/TMS; δppm): 8.86 (brs, 2H), 7.04 (d, 1H), 6.87 (d, 1H), 3.99 (s, 3H), 3.95 (s, 3H), 2.48 (s, 6H)

PREPARATION EXAMPLE 42

Synthesis of methyl 4,7-dimethyl-3-((methylthio)thio-carbonyl)indole-2-carboxylate (compound 42)

1) Synthesis of 4,7-dimethyl-3-((methylthio)thio-carbonyl)indole-2-carboxylic acid (intermediate compound) 3.6 g (158 mmol) of sodium hydride was placed in a flask dried with heating. Thereto was added 30 ml of anhydrous tetrahydrofuran (THF). After the reaction mixture was cooled to 0° C., 50 ml of a solution of 4.0 g (20 mmol) of methyl 4,7-dimethylindole-2-carboxylate in anhydrous THF was added dropwise over a period of 15 minutes. The reaction mixture was refluxed for 30 minutes. After addition of 4.6 g of carbon disulfide, the reaction mixture was further refluxed for 4 hours. The reaction mixture was gradually poured into ice water and filtered. Then 2.6 g of dimethyl sulfate was added dropwise to the filtrate and the reaction mixture was stirred for 20 minutes. The reaction mixture was made acid with 6N HCl aqueous solution and extracted with 30 ml of ethyl acetate three times. The ethyl acetate layers were collected, dried over anhydrous magnesium sulfate and concentrated under reduced pressure. The solids thus obtained were washed with chloroform to provide 480 mg of yellow crystals. Yield: 9%

2) Synthesis of methyl 4,7-dimethyl-3-((methyl-thio)thiocarbonyl)indole-2-carboxylate (compound 42)

A solution of 200 mg (0.27 mmol) of the above 4,7-dimethyl-3-((methylthio)thiocarbonyl)indole-2-carboxylic acid in 50 ml of methanol was prepared. While the solution was stirred at room temperature, 7 ml of trimethylsilyldiazomethane was added dropwise. The reaction mixture was stirred for 15 minutes and dried under reduced pressure. The residue was purified by silica gel column chromatography to provide 180 mg of light red crystals. Yield: 86% m.p.: 163°–164° C.; $^1$H-NMR (300 MHz, CDCl$_3$/TMS; δppm): 8.78 (brs, 1H), 7.03 (d, 1H), 6.82 (d, 1H), 3.87 (s, 3H), 2.89 (s, 3H), 2.47 (s, 6H)

PREPARATION EXAMPLE 43

Synthesis of methyl 4,7-dimethyl-3-(phenyliminomethyl)indole-2-carboxylate (compound 43)

A solution of 0.8 g (3.5 mmol) of methyl 3-formyl-4,7-dimethylindole-2-carboxylate in 20 ml of methanol was prepared. Thereto was added 0.5 g (5.2 mmol) of aniline. The reaction mixture was stirred at 60° C. for 2 hours and then cooled to room temperature. The crystals precipitated were separated by filtration, washed with water and dried under reduced pressure to provide 690 mg of yellow crystals. Yield: 65% m.p.: 128°–129° C.; $^1$H-NMR (300 MHz, CDCl$_3$/TMS; δppm): 9.26 (brs, 1H), 8.78 (s, 1H), 7.61–7.20 (m, 5H), 7.07 (d, 1H), 6.95 (d, 1H), 4.00 (s, 3H), 2.77 (s, 3H), 2.51 (s, 3H)

PREPARATION EXAMPLE 44

Synthesis of methyl 4,7-dimethyl-3-(methyliminomethyl)-indole-2-carboxylate (compound 44)

The title compound was prepared in the same manner as in Preparation Example 43 except that methylamine was used in place of aniline. Yield: 10% m.p.: 261°–262° C.; $^1$H-NMR (300 MHz, CDCl$_3$/TMS; δppm): 12.40 (brs, 1H), 10.36 (s, 1H), 10.13 (brs, 1H), 7.00 (d, 1H), 6.95 (d, 1H), 3.32 (s, 3H), 2.92 (d, 3H), 2.65 (s, 3H), 2.52 (s, 3H)

PREPARATION EXAMPLE 45

Synthesis of methyl 4,7-dimethyl-3-(benzyliminomethyl)-indole-2-carboxylate (compound 44) indole-2-carboxylate (compound 45)

The title compound was prepared in the same manner as in Preparation Example 43 except that benzylamine was used in place of aniline. Yield: 32.0%

$^1$H-NMR (300 MHz, CDCl$_3$/TMS; δppm): 8.13 (s, 1H), 8.70 (brs, 1H), 7.02 (d, 1H), 6.89 (d, 1H), 6.34 (s, 2H), 3.99 (s, 3H), 2.67 (s, 3H), 2.46 (s, 3H)

PREPARATION EXAMPLE 46

Synthesis of methyl 3-cyano-4,7-dimethylindole-2-carboxylate (compound 46)

15 ml of a solution of 450 mg (1.83 mmol) of methyl 3-(hydroxyiminomethyl)-4,7-dimethylindole-2-carboxylate in diethyl ether was prepared. 15 ml of a solution of 435 mg (3.66 mmol) of thionyl chloride in diethyl ether was added dropwise thereto at 0° C. over a period of 5 minutes. Diethyl ether was removed under reduced pressure. To remove thionyl chloride, 15 ml of benzene was added and the reaction mixture was concentrated under reduced pressure. The residue was purified by silica gel column chromatography to provide 100 mg of white crystals. Yield: 24% m.p.: 145°–146° C.; $^1$H-NMR (300 MHz, CDCl$_3$/TMS; δppm): 8.66 (brs, 1H), 7.03 (d, 1H), 6.74 (d, 1H), 3.95 (s, 3H), 2.65 (s, 3H), 2.45 (s, 3H)

PREPARATION EXAMPLE 47

Synthesis of methyl 3-(hydroxyiminomethyl)-4,7-dimethylindole-2-carboxylate (compound 47)

A solution of 0.7 g (3.03 mmol) of methyl 4,7-dimethylindole-2-carboxylate in 15 ml of ethanol was prepared. An aqueous solution (7.5 ml) containing 0.43 g (5.21 mmol) of sodium acetate and 0.22 g (3.075 mmol) of hydroxylamine hydrochloride was added thereto and the reaction mixture was refluxed for 4 hours. After ethanol was distilled off under reduced pressure, the residue was poured into 100 ml of water. The crude crystals were separated by suction filtration and dried with heating under vacuum to provide 690 mg of white crystals. Yield: 93% m.p.: 183°–184° C.; $^1$H-NMR (300 MHz, CDCl$_3$/TMS; δppm): 9.96 (brs, 1H), 9.86 (s, 1H), 7.84 (brs, 1H), 7.08 (d, 1H), 6.99 (d, 1H), 4.05 (s, 3H), 2.78 (s, 3H), 2.50 (s, 3H)

PREPARATION EXAMPLE 48

Synthesis of methyl 3-(methoxyiminomethyl)-4,7-dimethylindole-2-carboxylate (compound 48)

A mixture of 0.8 g (3.25 mmol) of methyl 3-(hydroxyiminomethyl)-4,7-dimethylindole-2-carboxylate, 0.60 g (4.23 mmol) of methyl iodide, 0.59 g (4.23 mmol) of potassium carbonate and 20 ml of acetonitrile was refluxed for 19 hours. After potassium carbonate was removed by filtration, acetonitrile was distilled off under reduced pressure. The residue was dissolved in ethyl acetate, washed with water three times and dried over anhydrous magnesium sulfate. The crude crystals were purified by silica gel column chromatography to provide 210 mg of light yellow crystals. Yield: 25% m.p.: 107°–108° C.; $^1$H-NMR (300 MHz, CDCl$_3$/TMS; δppm): 8.93 (brs, 1H), 8.81 (s, 1H), 7.03 (d, 1H), 6.88 (d, 1H), 4.01 (s, 3H), 3.98 (s, 3H), 2.68 (s, 3H), 2.47 (s, 3H)

PREPARATION EXAMPLE 49

Synthesis of methyl 4,7-dimethyl-3-(propargyloxyimino-methyl)indole-2-carboxylate (compound 49)

The title compound was prepared in the same manner as in Preparation Example 48 except that propargyl bromide was used in place of methyl iodide. Yield: 10% m.p.: 113°–114° C.; $^1$H-NMR (300 MHz, CDCl$_3$/TMS; δppm): 8.96 (brs, 1H), 8.91 (s, 1H), 7.04 (d, 1H), 6.89 (d, 1H), 4.78 (d, 2H), 3.98 (s, 3H), 2.71 (s, 3H), 2.50 (t, 1H), 2.47 (s, 3H)

PREPARATION EXAMPLE 50

Synthesis of methyl 3-(benzyloxyiminomethyl)-4,7-dimethylindole-2-carboxylate (compound 50)

The title compound was prepared in the same manner as in Preparation Example 48 except that benzyl chloride was used in place of methyl iodide. Yield: 23% m.p.: 104°–105° C.; $^1$H-NMR (300 MHz, CDCl$_3$/TMS; δppm): 9.63 (brs, 1H), 8.91 (s, 1H), 7.44–7.29 (m, 5H), 6.98 (d, 1H), 6.82 (d, 1H), 5.22 (s, 2H), 3.92 (s, 3H), 2.51 (s, 3H), 2.45 (s, 3H)

PREPARATION EXAMPLE 51

Synthesis of methyl 3-(acetoxyiminomethyl)-4,7-dimethylindole-2-carboxylate (compound 51)

A solution of 0.8 g (3.3 mmol) of methyl 3-(hydroxyiminomethyl)-4,7-dimethylindole-2-carboxylate in 15 ml of anhydrous THF was cooled to 0° C., and then 0.5 ml (3.6 mmol) of triethylamine was added. While the reaction mixture was stirred at 0° C., a solution of 0.25 ml (3.6 mmol) of acetyl chloride in 5 ml of THF was added dropwise over a period of 15 minutes. The reaction mixture was stirred at room temperature for 1 hour and then poured into 100 ml of ice water. The crystals were separated by filtration and dried to provide 0.85 g of yellow crystals.

Yield: quantitative m.p.: 161°–162° C.; $^1$H-NMR (300 MHz, CDCl$_3$/TMS; δppm): 11.1 (brs, 1H), 9.26 (s, 1H), 7.03 (d, 1H), 6.76 (d, 1H), 3.98 (s, 3H), 2.70 (s, 3H), 2.36 (s, 3H), 2.33 (s, 3H)

PREPARATION EXAMPLE 52

Synthesis of methyl 3-aminomethyl-4,7-dimethylindole-2-carboxylate (compound 52)

A solution of 1.5 g of methyl 3-(hydroxyimino-methyl)-4,7-dimethylindole-2-carboxylate in 200 ml of chloroform-ethanol (1:1) was prepared and 100 mg of platinum oxide was added. The air in the reaction system was substituted with hydrogen and the reaction mixture was stirred vigorously. After completion of the reaction, the reaction mixture was subjected to Celite filtration, and the filtrate was concentrated under reduced pressure. The residue was purified by silica gel column chromatography to provide yellow crystals. Yield: 50%

$^1$H-NMR (300 MHz, CDCl$_3$/TMS; δppm): 8.30 (brs, 1H), 6.96 (d, 2H), 6.73 (d, 1H), 5.00 (brs, 2H), 3.94 (s, 3H), 3.56 (brs, 2H), 2.72 (s, 3H), 2.52 (s, 3H)

PREPARATION EXAMPLE 53

Synthesis of methyl 3-methylthio(thiocarbonyl) aminomethyl-4,7-dimethylindole-2-carboxylate (compound 53)

A mixed solution of 0.72 g of methyl 3-aminomethyl-4,7-dimethylindole-2-carboxylate, 1.2 ml of pyridine and 0.61 ml of triethylamine was prepared and 0.3 ml of carbon disulfide was added at 0° C. After the reaction mixture was stirred at 0° C. for 1 hour, 0.312 ml (0.27 mmol) of methyl iodide was added and stirring was continued at 7° C. for 24 hours. The reaction mixture was added dropwise to 100 ml of a 1.5N sulfuric acid aqueous solution and then extracted with 20 ml of diethyl ether three times. The ether layers were combined, dried over anhydrous magnesium sulfate and concentrated under reduced pressure. The crystals thus obtained were purified by silica gel column chromatography to provide 80 mg of white crystals. Yield: 50% m.p.: 183°–184° C.; $^1$H-NMR (300 MHz, CDCl$_3$/TMS; δppm): 10.9 (brs, 1H), 10.51 (s, 1H), 6.95 (d, 1H), 6.75 (d, 1H), 5.98 (s, 2H), 3.94 (s, 3H), 2.58 (s, 3H), 2.51 (s, 6H)

PREPARATION EXAMPLE 54

Synthesis of methyl 3-hydroxymethyl-4,7-dimethylindole-2-carboxylate (compound 54)

A solution of 4.5 g (19.5 mmol) of methyl 3-formyl-4,7-diemthylindole-2-carboxylate in 2.0 l of methanol was prepared and 2.0 g (52.9 mmol) of sodium borohydride was added at room temperature over a period of 10 minutes. The reaction mixture was stirred for 30 minutes and 500 ml of water was added. Methanol was distilled off under reduced pressure, and the residue was extracted with 150 ml of ethyl acetate three times. The ethyl acetate solution thus obtained was dried over magnesium sulfate and concentrated under reduced pressure. The solids thus obtained were purified by silica gel column chromatography (n-hexane: ethyl acetate=1:1) to provide 3.84 g of light yellow crystals. Yield: 85% m.p.: 197°–198° C.; $^1$H-NMR (300 MHz, CDCl$_3$/TMS; δppm): 8.68 (brs, 1H), 7.01 (d, 1H), 6.84 (d, 1H), 5.23 (d, 2H), 4.00 (s, 3H), 2.74 (s, 3H), 2.46 (s, 3H)

PREPARATION EXAMPLE 55

Synthesis of methyl 3-acetoxymethyl-4,7-dimethylindole-2-carboxylate (compound 55)

A solution of 0.8 g of methyl 3-hydroxymethyl-4,7-dimethylindole-2-carboxylate in 10 ml of pyridine was prepared and 0.45 ml of acetic anhydride was added. The reaction mixture was stirred overnight and then poured into 100 ml of ice water. The reaction mixture was acidified with 1N HCl aqueous solution and extracted with 20 ml of ethyl acetate three times. The ethyl acetate layers were combined, dried over anhydrous magnesium sulfate and concentrated under reduced pressure to provide 200 mg of light yellow crystals. Yield: 22% m.p.: 171°–172° C.; $^1$H-NMR (300 MHz, CDCl$_3$/TMS; δppm): 9.03 (brs, 1H), 7.02 (d, 1H), 6.86 (d, 1H), 5.73 (d, 2H), 3.98 (s, 3H), 2.54 (s, 3H), 2.47 (s, 3H), 2.09 (s, 3H)

PREPARATION EXAMPLE 56

Synthesis of methyl 3-chloro-4,7-dimethylindole-2-carboxylate (compound 56)

A solution of 5.0 g (24.6 mmol) of methyl 4,7-dichloroindole-2-carboxylate in 100 ml of anhydrous chloroform was cooled to 0° C. After addition of 7.5 g of phosphorus pentachloride in three divided portions, the reaction mixture was refluxed for about 40 minutes. The reaction mixture was poured into 400 ml of ice water and extracted with 100 ml of chloroform three times. The chloroform layers were combined and dried over anhydrous magnesium sulfate and concentrated under reduced pressure to provide 5.4 g of white crystals. Yield: quantitative m.p.: 115°–116° C.

$^1$H-NMR (300 MHz, CDCl$_3$/TMS; δppm): 8.71 (brs, 1H), 7.00 (d, 1H), 6.81 (d, 1H), 3.99 (s, 3H), 2.77 (s, 3H), 2.43 (s, 3H)

PREPARATION EXAMPLE 57

Synthesis of methyl 3-bromo-4,7-dimethylindole-2-carboxylate (compound 57)

A solution of 1.0 g (4.9 mmol) of methyl 4,7-dimethylindole-2-carboxylate in 22 ml of DMF was cooled to 0° C. A solution of 1.03 g (9.8 mmol) of N-bromosuccinimide in 52 ml of DMF was added dropwise at 0° C. over a period of 1 hour and the reaction mixture was stirred for 30 minutes. The reaction mixture was poured into 400 ml of ice water, acidified with a 1N HCl aqueous solution and extracted with 100 ml of ethyl acetate three times. The ethyl acetate layers were combined, dried over anhydrous magnesium sulfate and concentrated under reduced pressure. The residue was purified by silica gel chromatography to provide 510 mg of yellow crystals. Yield: 36% m.p.: 173°–174° C.; $^1$H-NMR (300 MHz, CDCl$_3$/TMS; δppm): 8.88 (brs, 1H), 6.95 (d, 1H), 6.85 (d, 1H), 3.96 (s, 3H), 2.87 (s, 3H), 2.48 (s, 3H)

PREPARATION EXAMPLE 58

Synthesis of methyl 3-carbamoyl-4,7-dimethylindole-2-carboxylate (compound 58)

A solution of 2.0 g (9.9 mmol) of methyl 4,7-dimethylindole-2-carboxylate in 200 ml of anhydrous acetonitrile was cooled to 0° C. A solution of 3 ml (9.9 mmol) of chlorosulfonylisocyanate in 50 ml of anhydrous acetonitrile was added dropwise over a period of 15 minutes and the reaction mixture was stirred at room temperature for 30 minutes. After distilling off acetonitrile under reduced pressure, the residue was dissolved in 15 ml of acetonitrile-water (4:1). The pH of the solution was adjusted to 8 by gradually adding 10% potassium hydroxide aqueous solution dropwise. The white crystals precipitated were separated by filtration and air-dried and then dried under reduced pressure to provide 1.0 g of white crystals.

Yield: 42% m.p.: 201°–202° C.; $^1$H-NMR (300 MHz, CDCl$_3$/TMS; δppm): 10.86 (brs, 1H), 7.23 (brs, 1H), 6.95 (d, 1H), 6.79 (d, 1H), 6.66 (brs, 1H), 3.93 (s, 3H), 2.59 (s, 3H), 2.51 (s, 3H)

PREPARATION EXAMPLE 59

Synthesis of methyl 3-acetyl-4-chloro-7-methylindole-2-carboxylate (compound 59)

To 10 ml of anhydrous acetonitrile were added 0.74 ml (12.9 mmol) of acetic acid and 0.4 g of polyphosphoric acid. After the air in the reaction system was replaced with nitrogen, 1.86 ml (12.9 mmol) of trifluoroacetic anhydride was added and the reaction mixture was stirred at room temperature for 10 minutes. 10 ml of a solution of 1.0 g (4.3 mmol) of methyl 4-chloro-7-methylindole-2-carboxylate in acetonitrile was added dropwise over a period of 15 minutes and the reaction mixture was stirred at room temperature for 5 hours. The reaction mixture was poured into 100 ml of ice water and extracted with 15 ml of ethyl acetate three times. The extract was dried over anhydrous magnesium sulfate and concentrated under reduced pressure. The crude crystals were purified by silica gel column chromatography to provide 270 mg of white crystals. Yield: 25% m.p.: 167°–168° C.; $^1$H-NMR (300 MHz, CDCl$_3$/TMS; δppm): 8.91 (brs, 1H), 7.06 (d, 1H), 7.02 (d, 1H), 3.97 (s, 3H), 2.72 (s, 3H), 2.50 (s, 3H)

PREPARATION EXAMPLE 60

Synthesis of methyl 3-acetyl-4,7-dimethylindole-2-carboxylate (compound 60)

The title compound was prepared in the same manner as in Preparation Example 59 except that methyl 4,7-dimethylindole-2-carboxylate was used in place of methyl 4-chloro-7-methylindole-2-carboxylate. White crystals were obtained. Yield: 30%

$^1$H-NMR (300 MHz, CDCl$_3$/TMS; δppm): 8.81 (s, 1H), 7.04 (d, 1H), 6.85 (d, 1H), 3.95 (s, 3H), 2.69 (s, 3H), 2.47 (s, 3H), 2.41 (s, 3H)

PREPARATION EXAMPLE 61

Synthesis of methyl 4-chloro-7-methyl-3-nitroindole-2-carboxylate (compound 61)

100 ml of a solution of 2.0 g (8.95 mmol) of methyl 4-chloro-7-methylindole-2-carboxylate in chloroform was prepared and 2 ml of fuming nitric acid (specific gravity: 1.62) was gradually added dropwise at 0° C. The reaction mixture was stirred for 15 minutes and then poured into 100 ml of ice water. The reaction mixture was extracted with 20 ml of ethyl acetate three times. The ethyl acetate layers were dried over anhydrous magnesium sulfate and concentrated under reduced pressure. The solids thus obtained were purified by silica gel column chromatography to provide 800 mg of yellow crystals.

Yield: 36% m.p.: 174°–175° C.; $^1$H-NMR (300 MHz, CDCl$_3$/TMS; δppm): 9.10 (brs, 1H), 7.16 (d, 1H), 7.13 (d, 1H), 3.99 (s, 3H), 2.52 (s, 3H)

PREPARATION EXAMPLE 62

Synthesis of methyl 4,7-dimethyl-3-nitroindole-2-carboxylate (compound 62)

The title compound was prepared in the same manner as in Preparation Example 61 except that methyl 4,7-dimethylindole-2-carboxylate was used in place of methyl 4-chloro-7-methylindole-2-carboxylate. Yellow crystals were obtained. Yield: 50% m.p.: 193°–194° C.; $^1$H-NMR (300 MHz, CDCl$_3$/TMS; δppm): 9.76 (brs, 1H), 7.12 (d, 1H), 6.98 (d, 1H), 4.01 (s, 3H), 2.59 (s, 3H), 2.58 (s, 3H)

PREPARATION EXAMPLE 63

Synthesis of methyl 3-amino-4,7-dimethylindole-2-carboxylate (compound 63)

A solution of 2.5 g (0.01 mol) of methyl 4,7-dimethyl-3-nitroindole-2-carboxylate in 600 ml of ethyl acetate-acetic acid (1:1) was prepared. A suspension of 28.2 g (504 mmol) of iron powder in 200 ml of 5% acetic acid aqueous solution was heated to 70° C. and the above solution was added dropwise thereto over a period of 1.5 hours. After completion of the addition, the reaction mixture was stirred for 40 minutes and then subjected to Celite filtration. After addition of 300 ml of water, the filtrate was extracted with 250 ml of ethyl acetate three times. The extract was back-extracted with 0.5N HCl aqueous solution three times. The pH of the aqueous solution thus obtained was adjusted to 12 with 10% sodium hydroxide aqueous solution and then extracted with 300 ml of diethyl ether three times. The diethyl ether layers were combined, dried over anhydrous magnesium sulfate and concentrated under reduced pressure. The solids thus obtained were purified by silica gel column chromatography (n-hexane:ethyl acetate=2:1) to provide 1.8 g of yellow crystals. Yield: 83% m.p.: 171°–173° C.; $^1$H-NMR (300 MHz, CDCl$_3$/TMS; δppm): 7.63 (brs, 1H), 6.95 (d, 1H), 6.54 (d, 1H), 4.97 (brs, 2H), 3.93 (s, 3H), 2.70 (s, 3H), 2.37 (s, 3H)

PREPARATION EXAMPLE 64

Synthesis of methyl 3-acetylamino-4,7-dimethylindole-2-carboxylate (compound 64)

A mixture of 0.6 g (2.75 mmol) of methyl 3-amino-4,7-dimethylindole-2-carboxylate, 0.22 ml (3.3 mmol) of pyridine and 15 ml of anhydrous THF was cooled to 0° C. 10 ml of a solution of 0.24 ml (3.3 mmol) of acetyl chloride in anhydrous THF was added dropwise over a period of 30 minutes. After completion of the addition, the reaction mixture was stirred for 30 minutes. The reaction mixture was poured into 200 ml of water and extracted with 30 ml of ethyl acetate three times. The ethyl acetate layers were combined, washed with 100 ml of water once, dried over anhydrous magnesium sulfate and concentrated under reduced pressure. The residue was recrystallized from ethyl acetate to provide 200 mg of white crystals. Yield: 28% m.p.: 221°–222° C.; $^1$H-NMR (300 MHz, DMSO-d$_6$/TMS; δppm): 10.61 (brs, 1H), 8.98 (brs, 1H), 6.91 (d, 1H), 6.70 (d, 1H), 3.90 (s, 3H), 2.54 (s, 3H), 2.48 (s, H), 2.20 (s, 3H)

PREPARATION EXAMPLE 65

Synthesis of methyl 4,7-dimethyl-3-((methylaminocarbonyl)amino)indole-2-carboxylate (compound 65)

A mixture of 0.6 g (2.75 mmol) of methyl 3-amino-4,7-dimethylindole-2-carboxylate, one drop of pyridine and 15 ml of anhydrous THF was prepared and 5.0 ml of methyl isocyanate was added dropwise at 0° C. The reaction mixture was stirred at room temperature for 2.5 hours. The crystals precipitated were separated by filtration, washed with ethyl acetate and air-dried to provide 180 mg of white crystals. Yield: 24% m.p.: 230° C. (decomposed); $^1$H-NMR (300 MHz, DMSO-d$_6$/TMS; δppm): 11.25 (brs, 1H), 7.55 (s, 1H), 6.88 (d, 1H), 6.65 (d, 1H), 6.12 (brs, 1H), 3.84 (s, 3H), 2.62 (d, 3H), 2.48 (s, 3H), 2.44 (s, 3H)

PREPARATION EXAMPLE 66

Synthesis of methyl 3-((methoxycarbonyl)amino)-4,7-dimethylindole-2-carboxylate (compound 66)

A mixture of 0.6 g (2.75 mmol) of methyl 3-amino-4,7-dimethylindole-2-carboxylate, 0.22 ml (3.3 mmol) of pyridine and 15 ml of anhydrous THF was prepared. 10 ml of a solution of 0.26 ml (3.3 mmol) of methyl chloroformate in anhydrous THF was added dropwise at 0° C. over a period of 15 minutes and the reaction mixture was stirred for 1 hour. The reaction mixture was poured into 150 ml of ice water and extracted with 30 ml of ethyl acetate three times. The ethyl acetate layers were combined, dried over anhydrous magnesium sulfate and concentrated under reduced pressure. The solids thus obtained were recrystallized from ethyl acetate to provide 600 mg of red crystals. Yield: 79% m.p.: 184°–185° C.; $^1$H-NMR (300 MHz, DMSO-d$_6$/TMS; δppm): 8.64 (brs, 1H), 6.98 (d, 1H), 6.80 (d, 1H), 6.63 (brs, 1H), 3.92 (s, 3H), 3.79 (brs, 3H), 2.59 (s, 3H), 2.42 (s, 3H)

PREPARATION EXAMPLE 67

Synthesis of methyl 4,7-dimethyl-3-methylsulfenylindole-2-carboxylate (compound 67)

Under ice-cooling, 0.89 ml (7.4 mmol) of dimethyl disulfide was dissolved in 20 ml of 1,2-dichloroethane, and 0.53 ml (6.5 mmol) of sulfuryl chloride was added. The reaction mixture was stirred for 20 minutes and a solution of 2.00 g (9.8 imnol) of methyl 4,7-dimethylindole-2-carboxylate in 10 ml of anhydrous DMF was added. The reaction mixture was stirred for 2 hours, then dissolved in ethyl acetate and washed with water. The ethyl acetate layer was dried over anhydrous magnesium sulfate and concentrated under reduced pressure. The residue was purified by silica gel column chromatography to provide 1.94 g of white crystals. Yield: 80% m.p.: 82°–85° C.; $^1$H-NMR (300 MHz, CDCl$_3$/TMS; δppm): 8.91 (brs, 1H), 7.01 (d, 1H), 6.84 (d, 1H), 4.02 (s, 3H), 2.91 (s, 3H), 2.46 (s, 3H), 2.43 (s, 3H)

PREPARATION EXAMPLE 68

Synthesis of methyl 4,7-dimethyl-3-phenylsulfenylindole-2-carboxylate (compound 68)

A solution of 1.61 g (7.4 mmol) of diphenyldisulfide in 20 ml of 1,2-dichloroethane was prepared and 0.53 ml (6.5 mmol) of sulfuryl chloride was added at room temperature. After the reaction mixture was stirred for 20 minutes, a solution of 2.00 g (9.8 mmol) of methyl 4,7-dimethylindole-2-carboxylate in 10 ml of anhydrous DMF was added and the reaction mixture was stirred at room temperature for 2 hours. The reaction mixture was concentrated, dissolved in ethyl acetate and washed with water. The reaction mixture was dried over anhydrous magnesium sulfate and concentrated under reduced pressure. The residue was purified by silica gel column chromatography (toluene) to provide 2.70 g of white crystals. Yield: 88% m.p.: 159°–161° C.; $^1$H-NMR (300 MHz, CDCl$_3$/TMS; δppm): 9.18 (brs, 1H), 7.20–7.02 (m, 6H), 6.82 (d, 1H), 3.91 (s, 3H), 2.65 (s, 3H), 2.50 (s, 3H)

PREPARATION EXAMPLE 69

Synthesis of methyl 4,7-dimethyl-3-phenylsulfinylindole-2-carboxylate (compound 69)

A solution of 1.00 g (3.21 mmol) of methyl 4,7-dimethyl-3-phenylsulfenylindole-2-carboxylate (compound 68) in 10 ml of chloroform was prepared. Under ice-cooling, a solution of 1.24 g (3.21 mmol) of magnesium monoperoxyphthalate in 8 ml of methanol was added and the reaction mixture was stirred for 1.5 hours. The reaction mixture was extracted with chloroform, washed with aqueous saturated sodium chloride solution, dried over anhydrous magnesium sulfate and concentrated, thus giving 1.06 g of the title compound as white crystals. Yield: quantitative m.p.: 130°–131° C.; $^1$H-NMR (300 MHz, CDCl$_3$/TMS; δppm): 9.28 (brs, 1H), 7.53–7.34 (m, 5H), 7.07 (d, 1H), 6.88 (d, 1H), 3.98 (s, 3H), 2.51 (s, 3H), 2.31 (s, 3H); MS(m/z): 327(M$^+$)

PREPARATION EXAMPLE 70

Synthesis of methyl 4,7-dimethyl-3-phenylsulfonylindole-2-carboxylate (compound 70)

A solution of 0.50 g (1.61 mmol) of methyl 4,7-dimethyl-3-phenylsulfenylindole-2-carboxylate in 5 ml of chloroform was prepared. Under ice-cooling, 10 ml of a suspension of 1.03 g (4.01 mmol) of m-chloroperbenzoic acid in chloroform and 3 ml of methanol were added and the reaction mixture was stirred at room temperature for 1 hour. The reaction mixture was concentrated, dissolved in ethyl acetate and washed with aqueous sodium hydrogencarbonate solution. The reaction mixture was dried over anhydrous magnesium sulfate, concentrated and then recrystallized from methanol-water, thus giving 0.40 g of beige crystals. Yield: 73% m.p.: 204°–205° C.; $^1$H-NMR (300 MHz, CDCl$_3$/TMS; δppm): 9.32 (brs, 1H), 8.12 (pseudo-d, 2H), 7.60–7.42 (m, 3H), 7.03 (d, 1H), 6.93 (d, 1H), 4.02 (s, 3H), 2.57 (s, 3H), 2.47 (s, 3H); MS(m/z):343(M+)

PREPARATION EXAMPLE 71

Synthesis of methyl 4,7-dimethyl-3-methylsulfonylindole-2-carboxylate (compound 71)

The title compound was prepared in the same manner as in Preparation Example 70 except that methyl 4,7-dimethyl-3-methylsulfenylindole-2-carboxylate was used in place of methyl 4,7-dimethyl-3-phenylsulfenylindole-2-carboxylate. The compound was obtained as yellowish brown solids. Yield: 55% m.p.: 163°–164° C.; $^1$H-NMR (300 MHz, CDCl$_3$/TMS; δppm): 9.57 (brs, 1H), 7.07 (d, 1H), 7.02 (d, 1H), 3.99 (s, 3H), 3.40 (s, 3H), 2.78 (s, 3H), 2.47 (s, 3H); MS(m/z):281 (M+)

PREPARATION EXAMPLE 72

Synthesis of ethyl 3-methoxycarbonyl-4,7-dimethylindole-2-carboxylate (compound 72)

The title compound was prepared in the same manner as in Preparation Example 38 except that 3-methoxycarbonyl-4,7-dimethylindole-2-carboxylic acid was used in place of 4-chloro-7-methyl-3-methoxycarbonylindole-2-carboxylic acid. The compound was obtained as white crystals. Yield: 92.0% m.p.: 128°–129° C.; $^1$H-NMR (300 MHz, CDCl$_3$/TMS; δppm): 8.91 (brs, 1H), 7.03 (d, 1H), 6.86 (d, 1H), 4.41 (q, 2H), 3.97 (s, 3H), 2.48 (s, 3H), 2.47 (s, 3H), 1.42 (t, 3H)

PREPARATION EXAMPLE 73

Synthesis of methyl 3-(benzothiazol-2-yl)-4,7-dimethylindole-2-carboxylate (compound 73)

In 10 ml of ethyl acetate were dissolved 0.50 g (2.16 mmol) of methyl 3-formyl-4,7-dimethylindole-2-carboxylate and 0.27 g (2.16 mmol) of o-aminothiophenol. The reaction mixture was stirred at room temperature overnight. After addition of 0.30 g of o-aminothiophenol, the reaction mixture was stirred for 1 day and then poured into water. The reaction mixture was extracted with diethyl ether, washed with water and concentrated. The crude crystals were purified by silica gel column chromatography (toluene) and recrystallized from methanol-water to provide 0.15 g of beige powder. Yield: 20% m.p.: 193°–194° C.; $^1$H-NMR (300 MHz, CDCl$_3$/TMS; δppm): 9.05 (brs, 1H), 8.14 (d, 1H), 7.95 (d, 1H), 7.55 (pseudo-t, 1H), 7.46 (pseudo-t, 1H), 7.07 (d, 1H), 6.84 (d, 1H), 3.74 (s, 3H), 2.53 (s, 3H), 2.10 (s, 3H)

PREPARATION EXAMPLE 74

Synthesis of methyl 3-(2-(methoxycarbonyl)vinyl)-4,7-dimethylindole-2-carboxylate (compound 74)

In 23 ml of anhydrous acetonitrile were dissolved 1.5 g (7.4 mmol) of methyl 4,7-dimethylindole-2-carboxylate and 7.6 ml of methyl acrylate. The air in the reaction system was substituted with nitrogen. After cooling the reaction mixture to 0° C., 1.66 g (7.4 mmol) of palladium acetate was added and the reaction mixture was stirred for 30 minutes. Stirring was further continued at room temperature for 19 hours. After addition of 60 ml of acetonitrile, the reaction mixture was subjected to Celite filtration. The filtrate was concentrated under reduced pressure and the solids thus obtained were purified by silica gel column chromatography to provide 680 mg of yellow crystals. Yield: 48% m.p.: 135°–136° C.; $^1$H-NMR (300 MHz, CDCl$_3$/TMS; δppm): 8.99 (brs, 1H), 8.35 (d, 1H), 7.03 (d, 1H), 6.86 (d, 1H), 6.44 (d, 1H), 3.96 (s, 3H), 3.83 (s, 3H), 2.62 (s, 3H), 2.44 (s, 3H) MS(m/z):343(M+)

PREPARATION EXAMPLE 75

Synthesis of methyl 3-(2-(methoxycarbonyl)ethyl)-4,7-dimethylindole-2-carboxylate (compound 75)

A solution of 300 mg of methyl 3-(2-(methoxycarbonyl) vinyl)-4,7-dimethylindole-2-carboxylate in 20 ml of ethanol was prepared and 15 mg of platinum dioxide was added. Under nitrogen atmosphere, the reaction mixture was stirred for 2 hours. The reaction mixture was filtered through Celite 545 and concentrated under reduced pressure to provide 290 mg of yellow crystals. Yield: quantitative $^1$H-NMR (300 MHz, CDCl$_3$/TMS; δppm): 8.53 (s, 1H), 7.05 (d, 1H), 6.79 (d, 1H), 3.98 (s, 3H), 3.87 (s, 3H), 3.56 (d, 2H), 2.70 (s, 3H), 2.53 (t, 2H), 2.41 (s, 3H)

PREPARATION EXAMPLE 76

Synthesis of methyl 1-hydroxy-4,7-dimethylindole-2-carboxylate (compound 76)

A flask was charged with 1.0 g (4.9 mmol) of methyl 4,7-dimethylindoline-2-carboxylate and 64 mg (0.193 mmol) of sodium tungstate-dihydrate, and the air in the reaction system was substituted with nitrogen. Methanol (15 ml) was added and the reaction mixture was cooled to 0° C. Then 1.25 g of 30% aqueous hydrogen peroxide solution was added and the reaction mixture was stirred for 3 hours. Yield: 35.5% m.p.: 85°–86° C.; $^1$H-NMR (300 MHz, DMSO-d$_6$/TMS; δppm): 10.53 (brs, 1H), 7.26 (d, 1H), 6.94 (d, 1H), 6.77 (d, 1H), 3.98 (s, 3H), 2.72 (s, 3H), 2.47 (s, 3H)

PREPARATION EXAMPLE 77

Synthesis of methyl 1-methoxy-4,7-dimethylindole-2-carboxylate (compound 77)

1) Synthesis of methyl 4,7-dimethylindoline-2-carboxylate (intermediate compound)

A flask dried with heating was charged with 1.6 g (7.9 mmol) of methyl 4,7-dimethylindole-2-carboxylate and 3.8 g (158 mmol) of chipped magnesium. After addition of 400 ml of anhydrous methanol, the reaction mixture was stirred vigorously for 30 minutes. The flask was placed in an ice bath to cool the reaction mixture to 0° C., and the reaction mixture was stirred overnight. The reaction mixture was diluted with 300 ml of water, filtered and extracted with 100 ml of methylene chloride three times. The methylene chloride layers were combined, dried over anhydrous magnesium sulfate and concentrated under reduced pressure. The solids thus obtained were purified by silica gel column chromatography to provide 1.28 g of light red crystals. Yield: 79% m.p.: 80° C.

2) Synthesis of methyl 1-methoxy-4,7-dimethylindole-2-carboxylate (compound 77)

A flask was charged with 1.0 g (4.9 mmol) of methyl 4,7-dimethylindoline-2-carboxylate and 64 mg (0.193 mmol) of sodium tungstate-dihydrate, and the air in the reaction system was substituted with nitrogen. After 15 ml of methanol was added and the reaction mixture was cooled to 0° C., 1.25 g of 30% aqueous hydrogen peroxide solution was added and the reaction mixture was stirred for 3 hours. Then 1.1 g of potassium carbonate and 0.68 g of dimethyl sulfate were added dropwise and the reaction mixture was stirred at 0° C. for 1 hour. The reaction mixture was added dropwise to ice water and extracted with 15 ml of ethyl acetate three times. The ethyl acetate layers were combined, dried over anhydrous magnesium sulfate and concentrated under reduced pressure. The crystals thus obtained were purified by silica gel column chromatography to provide 400 mg of white crystals. Yield: 36% m.p.: 90°–91° C.; $^1$H-NMR (300 MHz, CDCl$_3$/TMS; δppm): 7.16 (s, 1H), 7.00 (d, 1H), 6.82 (d, 1H), 4.11 (s, 3H), 3.94 (s, 3H), 2.68 (s, 3H), 2.48 (s,3H)

PREPARATION EXAMPLE 78

Synthesis of methyl 1-acetoxy-4,7-dimethylindole-2-carboxylate (compound 78)

A solution of 0.3 g (1.37 mmol) of methyl 2-hydroxy-4,7-dimethylindole-2-carboxylate and 0.13 ml of pyridine in 20 ml of anhydrous THF was cooled, to 0° C. and 0.12 ml of acetyl chloride was gradually added dropwise. The reaction mixture was stirred for 1 hour and then added dropwise to ice water. The crystals were separated by filtration and dried under reduced pressure to provide 0.30 g of green crystals. Yield: 92% m.p.: 87°–88° C.; $^1$H-NMR (300 MHz, CDCl$_3$/TMS; δppm): 7.26 (s, 1H), 7.00 (d, 1H), 6.86 (d, 1H), 3.88 (s, 3H), 2.49 (s, 6H), 2.41 (s, 3H)

PREPARATION EXAMPLE 79

Synthesis of methyl 1-(methoxycarbonyloxy)-4,7-dimethylindole-2-carboxylate (compound 79)

The title compound was prepared in the same manner as in Preparation Example 78 except that methyl chlorocarbonate was used in place of acetyl chloride.

Yield: 30%; m.p.: 75°–80° C.; $^1$H-NMR (300 MHz, CDCl$_3$/TMS; δppm): 7.31 (s, 1H), 6.95 (d, 1H), 6.78 (d, 1H), 4.34 (s, 3H), 3.91 (s, 3H), 2.76 (s, 3H), 2.49 (s, 3H)

PREPARATION EXAMPLE 80

Synthesis of methyl 1-acetyl-4,7-dimethylindole-2-carboxylate (compound 80)

A suspension of 0.11 g (4.13 mmol) of sodium hydride in 10 ml of anhydrous DMF was prepared. A solution of 0.8 g (3.94 mmol) of 4,7-dimethylindole-2-carboxylate in 10 ml of anhydrous DMF was added thereto dropwise at 0° C. over a period of 30 minutes and the reaction mixture was stirred for 1 hour. Then a solution of 0.47 g (4.33 mmol) of acetyl chloride in 0.4 ml of anhydrous DMF was added dropwise, and the reaction mixture was stirred at room temperature for 12 hours. The reaction mixture was added dropwise to 300 ml of ice water, acidified with 1N HCl aqueous solution and extracted with ethyl acetate three times. The ethyl acetate solutions were combined, dried over anhydrous magnesium sulfate and concentrated under reduced pressure. The residue was purified by silica gel column chromatography to provide 212 mg of white crystals.

Yield: 22%; m.p.: 92°–93° C.; $^1$H-NMR (300 MHz, CDCl$_3$/TMS; δppm): 7.42 (s, 1H), 7.09 (d, 1H), 6.88 (d, 1H), 3.96 (s, 3H), 2.72 (s, 3H), 2.55 (s, 3H), 2.39 (s, 3H)

PREPARATION EXAMPLE 81

Synthesis of methyl 4,7-dimethyl-3-methylsulfinylindole-2-carboxylate (compound 81)

The title compound was prepared in the same manner as in Preparation Example 70 except that methyl 4,7-dimethyl-3-methylsulfenylindole-2-carboxylate was used in place of methyl 4,7-dimethyl-3-phenylsulfenyl-indole-2-carboxylate. The compound was obtained as white crystals.

Yield: 15%; m.p.: 127° C.; $^1$H-NMR (300 MHz, CDCl$_3$/TMS; δppm): 9.53 (brs, 1H), 7.08 (d, 1H), 6.99 (d, 1H), 3.97 (s, 3H), 3.07 (s, 3H), 2.86 (s, 3H), 2.49 (s, 3H)

PREPARATION EXAMPLE 82

Synthesis of methyl 4,7-dimethyl-1-(phenoxy-carbonyl)indole-2-carboxylate (compound 82)

A suspension of 1.2 g (50 mmol) of 60% sodium hydride in 100 ml of anhydrous DMF was prepared. A solution of 9.2 g (45.3 mmol) of methyl 4,7-dimethylindole-2-carboxylate in 150 ml of anhydrous DMF was added dropwise thereto over a period of 1 hour. The reaction mixture was stirred at room temperature for 1 hour and then cooled to 0° C. A solution of 6.25 ml (50.0 mmol) of phenyl chlorocarbonate in 20 ml of anhydrous DMF was added dropwise over a period of 30 minutes. The reaction mixture was stirred at room temperature for 15 hours and then added dropwise to 800 ml of ice water. The reaction mixture was extracted with 200 ml of ethyl acetate three times. The ethyl acetate layers were combined, washed with 300 ml of water twice and dried over anhydrous magnesium sulfate. After the ethyl acetate layers were distilled off under reduced pressure, the residue was recrystallized from acetone to provide 1.50 g of light yellow crystals. Yield: 10% m.p.: 83°–84° C.; $^1$H-NMR (300 MHz, CDCl$_3$/TMS; δppm): 7.34–7.50 (m, 6H), 7.10 (d, 1H), 6.97 (d, 1H), 3.95 (s, 3H), 2.57 (s, 3H), 2.48 (s, 3H)

PREPARATION EXAMPLE 83

Synthesis of methyl 4,7-dimethyl-1-(methoxy-carbonyl)indole-2-carboxylate (compound 83)

The title compound was prepared in the same manner as in Preparation Example 82 except that methyl chlorocarbonate was used in place of phenyl chlorocarbonate. The compound was obtained as white crystals. Yield: 30% m.p.: 75°–80° C.; $^1$H-NMR (90 MHz, CDCl$_3$/TMS; δppm): 7.31 (s, 1H), 6.95 (d, 1H), 6.78 (d, 1H), 4.34 (s, 3H), 3.91 (s, 3H), 2.76 (s, 3H), 2.49 (s, 3H)

FORMULATION EXAMPLE 1

| (25% Wettable powder) Component | parts by weight |
|---|---|
| Compound of the invention | 25 |
| White carbon | 45 |
| Diatomaceous earth | 16 |

-continued (25% Wettable powder)

| Component | parts by weight |
|---|---|
| Sodium higher alcohol sulfate | 2 |
| Sodium salt of β-naphthalene-sulfonic acid formalin condensate | 2 |
| Alkylphenylphenol sulfate | 10 |
| Total | 100 |

FORMULATION EXAMPLE 2

(20% Emulsifiable concentrate)

| Component | parts by weight |
|---|---|
| Compound of the invention | 20 |
| Polyoxyethylene styrylphenyl ether | 8 |
| Sodium dodecylbenzene sulfate | 4 |
| Xylene | 68 |
| Total | 100 |

FORMULATION EXAMPLE 3
(Emulsifiable concentrate)

Ten parts of the compound of the invention was dissolved in a mixture of 35 parts of xylene and 35 parts of N,N-dimethylformamide. To the solution were added 14 parts of polyoxyethylene styrylphenyl ether and 6 parts of calcium dodecylbenzene sulfonate. The resulting mixture was stirred to give a 10% emulsifiable concentrate.

FORMULATION EXAMPLE 4
(Wettable powder)

Twenty parts of the compound of the invention was added to a mixture of 4 parts of sodium lauryl sulfate, 2 parts of calcium lignin sulfonate, 20 parts of finely powdered synthetic hydrous silicon oxide and 54 parts of diatomaceous earth. The resulting mixture was stirred with a juice mixer, giving a 20% wettable powder.

FORMULATION EXAMPLE 5
(Granules)

To 5 parts of the compound of the invention were added 5 parts of finely powdered synthetic hydrous silicon oxide, 5 parts of sodium dodecylbenzene sulfonate, 30 parts of bentonite and 55 parts of clay, followed by through stirring. A suitable amount of water was added, and the resulting mixture was further stirred, granulated with a granulating machine and air-dried to give 5% granules.

FORMULATION EXAMPLE 6
(Dust)

One part of the compound of the invention was dissolved in a suitable amount of acetone. To the solution were added 5 parts of finely powdered synthetic hydrous silicon oxide, 0.3 part of acidic isopropyl phosphate and 93.7 parts of clay. The resulting mixture was stirred with a juice mixer, and the acetone was distilled off to give a 1% dust.

FORMULATION EXAMPLE 7
(Flowable suspension)

Twenty parts of the compound of the invention and 1.5 parts of sorbitan trioleate were admixed with 28.5 parts of an aqueous solution containing 2 parts of polyvinyl alcohol. The mixture was finely ground by a sand grinder (to a particle diameter of 3 μ or less). To the obtained powder was added 40 parts of an aqueous solution containing 0.05 part of xanthane gum and 0.1 part of aluminum magnesium silicate. Then, 10 part of propylene glycol was further added, and the resulting mixture was stirred to give a 20% aqueous suspension.

Test examples are given below to demonstrate that the compound of the invention has an effect of preventing the disease of plants.

TEST EXAMPLE 1
(Test against cucumber gray mold)

A 500 ppm diluted solution of the wettable powder obtained in Formulation Example 1 was sprayed on the stems and leaves of cucumber seedlings (Suzunarishiyo variety, one- or two-leaf stage) cultivated in pots (7.5 cm in diameter, 200 ml in capacity). After air-drying, the seedlings were inoculated with a spore suspension of *Botrytis cinerea* (pathogen of cucumber gray mold). Four days later, the severity of disease was checked by the eye to determine the percentage of lesion area in treated and untreated plots, and the control index was calculated by the following formula. The results are shown in Table 1. Test compound numbers in Table 1 correspond to the compound numbers in the Preparation Examples. Test Compounds A and E are the above Compounds (A) and (E), respectively.

$$\text{Control index } (\%) = \frac{\text{Percentage of lesion area in untreated plot} - \text{Percentage of lesion area in treated plot}}{\text{Percentage of lesion area in untreated plot}} \times 100$$

TABLE 1

| Test Compound No. | Concentration of Test Compound (ppm) | Control Index (%) |
|---|---|---|
| 1 | 500 | 100 |
| 2 | 500 | 96 |
| 3 | 500 | 98 |
| 4 | 500 | 100 |
| 6 | 500 | 100 |
| 9 | 500 | 90 |
| 13 | 500 | 100 |
| 17 | 500 | 100 |
| 18 | 500 | 100 |
| 20 | 500 | 98 |
| 21 | 500 | 100 |
| 25 | 500 | 100 |
| A | 500 | 20 |
| E | 500 | 25 |

TEST EXAMPLE 2
(Test against cucumber powdery mildew)

A 500 ppm diluted solution of the wettable powder obtained in Formulation Example 1 was sprayed on the stems and leaves of cucumber seedlings (Suzunarishiyo variety, one- or two-leaf stage) cultivated in pots (7.5 cm in diameter, 200 ml in capacity). After air-drying, the seedlings were inoculated with a spore suspension of *Schaerotheca fuliginea* (pathogen of cucumber powdery mildew). Ten days later, the control index was calculated in the same manner as in Test Example 1. The results are shown in Table 2. Test compound numbers in Table 2 correspond to the compound numbers in the Preparation Examples. Test Compounds A and D are the above Compounds (A) and (D), respectively.

TABLE 2

| Test Compound No. | Concentration of Test Compound (ppm) | Control Index (%) |
| --- | --- | --- |
| 1 | 500 | 100 |
| 3 | 500 | 100 |
| 4 | 500 | 100 |
| 6 | 500 | 100 |
| 9 | 500 | 98 |
| 10 | 500 | 98 |
| 13 | 500 | 100 |
| 17 | 500 | 100 |
| 18 | 500 | 100 |
| 20 | 500 | 98 |
| 23 | 500 | 100 |
| 25 | 500 | 100 |
| 27 | 500 | 92 |
| A | 500 | 60 |
| D | 500 | 45 |

TEST EXAMPLE 3
(Test against *Collectotrichum lagenarium*)

A 500 ppm diluted solution of the emulsifiable concentrate obtained in Formulation Example 2 was sprayed on the stems and leaves of cucumber seedlings (Suzunarishiyo variety, one- or two-leaf stage) planted in pots (7.5 cm in diameter, 200 ml in capacity). After air-drying, the seedlings were inoculated with a spore suspension of *Colletotrichum lagenarium* (pathogen of cucumber anthracnose). Seven days later, the control index was calculated in the same manner as in Test Example 1. The results are shown in Table 3. Test compound numbers in Table 3 correspond to the compound numbers in the Preparation Examples. Test Compounds A and D are the above Compounds (A) and (D), respectively.

TABLE 3

| Test Compound No. | Concentration of Test Compound (ppm) | Control Index (%) |
| --- | --- | --- |
| 2 | 500 | 100 |
| 3 | 500 | 98 |
| 4 | 500 | 96 |
| 6 | 500 | 100 |
| 8 | 500 | 100 |
| 13 | 500 | 100 |
| 17 | 500 | 100 |
| 22 | 500 | 100 |
| 24 | 500 | 100 |
| 27 | 500 | 90 |
| A | 500 | 30 |
| D | 500 | 20 |

TEST EXAMPLE 4
(Control effect on cucumber gray mold)

The wettable powder of the invention obtained in Formulation Example 4 was diluted to a predetermined concentration (500 ppm) and sprayed in a sufficient amount on cucumber seedlings (Suzunarishiyo variety) cultivated in a greenhouse for about two weeks. After air-drying, the first leaves were cut off and inoculated with mycelial disks punched out from a colony of BENOMYL- and THIOPHANATE-METHYL-resistant *Botrytis cinerea* incubated on a potato-saccharose-agar culture at 25° C. for 3 days. After allowing the inoculated leaves to stand at a humidity of 100% and a temperature of 25° C. for 3 days, the lesion diameter was measured and the control index of each test compound was calculated by the following equation. The results are shown in Table 4. Test compound numbers in Table 4 correspond to the compound numbers in the Preparation Examples. Test Compounds A and B are the above Compounds (A) and (B), respectively.

Control index (%) =

$$\left(1 - \frac{\text{Average lesion diameter in treated plot}}{\text{Average lesion diameter in untreated plot}}\right) \times 100$$

TABLE 4

| Test Compound No. | Concentration of Test Compound (ppm) | Control Index (%) |
| --- | --- | --- |
| 33 | 500 | 100 |
| 39 | 500 | 100 |
| 47 | 500 | 100 |
| 48 | 500 | 100 |
| 51 | 500 | 100 |
| 54 | 500 | 100 |
| 57 | 500 | 100 |
| 77 | 500 | 100 |
| A | 500 | 0 |
| D | 500 | 0 |
| F | 500 | 0 |
| G | 500 | 0 |

Test Compound F: BENOMYL
Test Compound G: THIOPHANATEMETHYL

Table 4 reveals that the compounds of the present invention exhibit high fungicidal effects on the fungicide-resistant *Botrytis cinerea*.

TEST EXAMPLE 5
(Control effect on cucumber powdery mildew)

The wettable powder of the compound of the invention obtained in Formulation Example 4 was diluted to a predetermined concentration (500 ppm) and sprayed in a sufficient amount on cucumber seedlings (Suzunarishiyo variety) cultivated in a greenhouse for about two weeks. After air-drying, the seedlings were spray-inoculated with a suspension of conidia of BENOMYL- and THIOPHANATE-resistant *Sphaerotheca fuliginea* and allowed to stand in a greenhouse. Ten days after the inoculation, the seedlings were examined for the symptom of disease. The incidence was rated according to the severity of lesion on the examined leaves. The control index of each test compound was calculated by the equation in TEST EXAMPLE 4. The results are shown in Table 5. Test compound numbers in Table 5 correspond to the compound numbers in the Preparation Examples. Test Compounds A and B are the above Compounds (A) and (B), respectively.

TABLE 5

| Test Compound No. | Concentration of Test Compound (ppm) | Control Index (%) |
| --- | --- | --- |
| 33 | 500 | 100 |
| 39 | 500 | 100 |
| 47 | 500 | 100 |
| 48 | 500 | 100 |
| 54 | 500 | 100 |
| 57 | 500 | 100 |
| 77 | 500 | 100 |
| A | 500 | 0 |

TABLE 5-continued

| Test Compound No. | Concentration of Test Compound (ppm) | Control Index (%) |
|---|---|---|
| D | 500 | 0 |
| F | 500 | 0 |
| G | 500 | 0 |

Test Compound F: BENOMYL
Test Compound G: THIOPHANATEMETHYL

As apparent from Table 5, the compounds of the present invention exhibit high fungicidal effects on the fungicide-resistant *Sphaerotheca fuliginea*.

We claim:

1. A fungicidal composition for agricultural or horticultural use comprising, in an amount effective to control fungi in agricultural or horticultural fields, an indole-2-carboxylic acid ester derivative represented by the formula

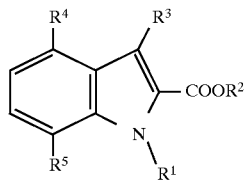

wherein $R^1$ is a hydrogen atom, a hydroxy group, a $C_{1-4}$acyl group, a $C_{1-4}$acyloxy group, a $C_{1-4}$alkoxy group, a $(C_{1-4}\text{alkoxycarbonyl})$oxy group, a phenoxycarbonyl group or a $C_{1-4}$alkoxycarbonyl group, $R^2$ is a $C_{1-4}$alkyl group, $R^3$ is a hydrogen atom, a $C_{1-4}$alkyl group, a $C_{2-4}$alkenyl group, a phenyl group, a cyano group, a carbamoyl group, a formyl group, a $C_{1-4}$acyl group, a carboxyl group, a $C_{1-4}$alkoxycarbonyl group, a hydroxyiminomethyl group, a $(C_{1-4}\text{alkoxyimino})$methyl group, a $(C_{2-4}\text{alkynyloxyimino})$methyl group, a $(C_{1-4}\text{acyloxyimino})$methyl group, a (N-phenylimino)methyl group, a (N-benzylimino)methyl group, an aminomethyl group, a $((C_{1-4}\text{alkylthio})\text{thiocarbonyl})$aminomethyl group, a $(C_{1-4}\text{alkylthio})$thiocarbonyl group, a nitro group, an amino group, a $C_{1-4}$acylamino group, a 3-$(C_{1-4}\text{alkyl})$ureido group, a $(C_{1-4}\text{alkoxycarbonyl})$amino group, a hydroxymethyl group, a $(C_{1-4}\text{acyloxy})$methyl group, a halogen atom, a 2-$(C_{1-4}\text{alkoxycarbonyl})$vinyl group, a 2-$(C_{1-4}\text{alkoxycarbonyl})$ethyl group, a benzothiazol-2-yl group, a $C_{1-4}$alkylsulfenyl group, a $C_{1-4}$alkylsulfinyl group, a $C_{1-4}$alkylsulfonyl group, a phenylsulfenyl group, a phenylsulfinyl group or a phenylsulfonyl group, $R^4$ and $R^5$ are the same or different and each represents a halogen atom, a $C_{1-4}$alkyl group, a $C_{1-4}$alkoxy group, a $C_{1-4}$haloalkyl group, a $C_{1-4}$haloalkoxy group, a benzyl group, a phenyl group, a cyano group, a nitro group, a $C_{1-4}$alkylsulfenyl group or a $C_{1-4}$alkylsulfonyl group, provided that when $R^1$ is a hydrogen atom, $R^3$ is a hydrogen atom, and $R^4$ is a methoxy group, $R^5$ must not be a bromine atom; and a suitable carrier.

2. A fungicidal composition for agricultural or horticultural use comprising, in an amount effective to control fungi in agricultural or horticultural fields, an indole-2-carboxylic acid ester derivative represented by the formula

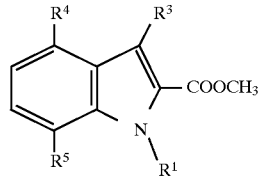

wherein $R^1$ is a hydrogen atom, a hydroxy group, a $C_{1-4}$acyl group, a $C_{1-4}$acyloxy group, a $C_{1-4}$alkoxy group, a $(C_{1-4}\text{alkoxycarbonyl})$oxy group, a phenoxycarbonyl group or a $C_{1-4}$alkoxycarbonyl group, $R^3$ is a $C_{1-4}$alkyl group, a $C_{2-4}$alkyl group, a phenyl group, a cyano group, a carbamoyl group, a formyl group, a $C_{1-4}$acyl group, a carboxyl group, a $C_{1-4}$alkoxycarbonyl group, a hydroxyiminomethyl group, a $(C_{1-4}\text{alkoxyimino})$methyl group, a $(C_{2-4}\text{alkynyloxyimino})$methyl group, a $(C_{1-4}\text{acyloxyimino})$methyl group, a (N-phenylimino)methyl group, a (N-benzylimino)methyl group, an aminomethyl group, a $((C_{1-4}\text{alkylthio})\text{thiocarbonyl})$aminomethyl group, a $(C_{1-4}\text{alkylthio})$thiocarbonyl group, a nitro group, an amino group, a $C_{1-4}$acylamino group, a 3-$(C_{1-4}\text{alkyl})$ureido group, a $(C_{1-4}\text{alkoxycarbonyl})$amino group, a hydroxymethyl group, a $(C_{1-4}\text{acyloxy})$methyl group, a halogen atom, a 2-$(C_{1-4}\text{alkoxycarbonyl})$vinyl group, a 2-$(C_{1-4}\text{alkoxycarbonyl})$ethyl group, a benzothiazol-2-yl group, a $C_{1-4}$alkylsulfenyl group, a $C_{1-4}$alkylsulfinyl group, a $C_{1-4}$alkylsulfonyl group, a phenylsulfenyl group, a phenylsulfinyl group or a phenylsulfonyl group, $R^4$ and $R^1$ are the same or different and each represents a halogen atom, a $C_{1-4}$alkyl group, a $C_{1-4}$alkoxy group, a $C_{1-4}$haloalkyl group, a $C_{1-4}$haloalkoxy group, a benzyl group, a phenyl group, a cyano group, a nitro group, a $C_{1-4}$alkylsulfenyl group or a $C_{1-4}$alkylsulfonyl group; and a suitable carrier.

3. A fungicidal composition for agricultural or horticultural use comprising, in an amount effective to control fungi in agricultural or horticultural fields, an indole-2-carboxylic acid ester derivative represented by the formula

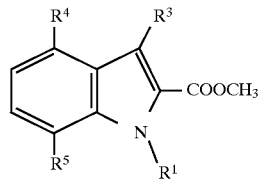

wherein $R^1$ is a hydrogen atom, a hydroxy group, a $C_{1-4}$acyl group, a $C_{1-4}$acyloxy group, a $C_{1-4}$alkoxy group, a $(C_{1-4}\text{alkoxycarbonyl})$oxy group, a phenoxycarbonyl group or a $C_{1-4}$alkoxycarbonyl group, $R^3$ is an alkoxyimino methyl group or an alkoxycarbonyl group, $R^4$ and $R^5$ are the same or different and each represents a halogen atom, a $C_{1-4}$alkyl group, a $C_{1-4}$alkoxy group, a $C_{1-4}$haloalkyl group, a $C_{1-4}$haloalkoxy group, a benzyl group, a phenyl group, a cyano group, a nitro group, a $C_{1-4}$alkylsulfenyl group or a $C_{1-4}$alkylsulfonyl group; and a suitable carrier.

4. A fungicidal composition for agricultural or horticultural use comprising, in an amount effective to control fungi in agricultural or horticultural fields, an indole-2-carboxylic acid ester derivative represented by the formula

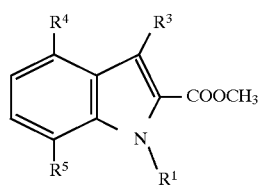

wherein $R^1$ is a hydrogen atom, a hydroxy group, a $C_{1-4}$acyl group, a $C_{1-4}$acyloxy group, a $C_{1-4}$alkoxy group, a ($C_{1-4}$alkoxycarbonyl)oxy group, a phenoxycarbonyl group or a $C_{1-4}$alkoxycarbonyl group, $R^3$ is a hydrogen atom, a $C_{1-4}$alkyl group, a $C_{2-4}$alkenyl group, a phenyl group, a cyano group, a carbamoyl group, a formyl group, a $C_{1-4}$acyl group, a carboxyl group, a $C_{1-4}$alkoxycarbonyl group, a hydroxyiminomethyl group, a ($C_{1-4}$alkoxyimino)methyl group, a ($C_{2-4}$alkynyloxyimino)methyl group, a ($C_{1-4}$acyloxyimino)methyl group, a (N-phenylimino)methyl group, a (N-benzylimino)methyl group, an aminomethyl group, a (($C_{1-4}$alkylthio)thiocarbonyl)aminomethyl group, a ($C_{1-4}$alkylthio)thiocarbonyl group, a nitro group, an amino group, a $C_{1-4}$acylamino group, a 3-($C_{1-4}$alkyl)ureido group, a ($C_{1-4}$alkoxycarbonyl)-amino group, a hydroxymethyl group, a ($C_{1-4}$acyloxy)methyl group, a halogen atom, a 2-($C_{1-4}$alkoxycarbonyl)vinyl group, a 2-($C_{1-4}$alkoxycarbonyl)-ethyl group, a benzothiazol-2-yl group, a $C_{1-4}$alkylsulfenyl group, a $C_{1-4}$alkylsulfinyl group, a $C_{1-4}$alkylsulfonyl group, a phenylsulfenyl group, a phenylsulfinyl group or a phenylsulfonyl group, $R^4$ is a halogen atom, a $C_{1-4}$alkyl group, a $C_{1-4}$haloalkyl group, a $C_{1-4}$haloalkoxy group, a benzyl group, a phenyl group, a cyano group, a $C_{1-4}$alkylsulfenyl group or a $C_{1-4}$alkylsulfonyl group, and $R^5$ is a halogen atom, a $C_{1-4}$alkyl group, a $C_{1-4}$alkoxy group, a $C_{1-4}$haloalkyl group, a $C_{1-4}$haloalkoxy group, a benzyl group, a phenyl group, a cyano group, a nitro group, a $C_{1-4}$alkylsulfenyl group or a $C_{1-4}$alkylsulfonyl group; and a suitable carrier.

5. A fungicidal composition for agricultural or horticultural use comprising, in an amount effective to control fungi in agricultural or horticultural fields, an indole-2-carboxylic acid ester derivative represented by the formula

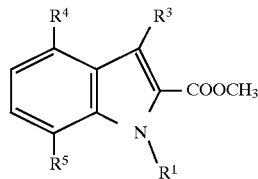

wherein $R^1$ is a hydrogen atom, $R^3$ is a hydrogen atom, $R^4$ is a $C_{1-4}$alkyl group, and $R^5$ is a $C_{1-4}$alkyl group; and a suitable carrier.

6. A fungicidal composition for agricultural or horticultural use comprising, in an amount effective to control fungi in agricultural or horticultural fields, an indole-2-carboxylic acid ester derivative represented by the formula

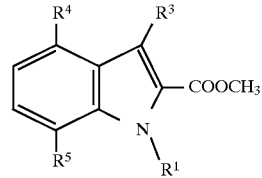

wherein $R^1$ is a hydrogen atom, $R^3$ is a hydrogen atom, $R^4$ is a halogen atom, and $R^5$ is a halogen atom; and a suitable carrier.

7. A fungicidal composition for agricultural or horticultural use comprising, in an amount effective to control fungi in agricultural or horticultural fields, an indole-2-carboxylic acid ester derivative represented by the formula

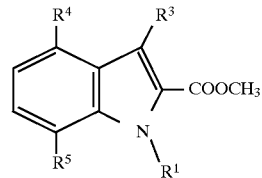

wherein $R^1$ is a hydrogen atom, $R^3$ is a hydrogen atom, $R^4$ is a $C_{1-4}$alkyl group, and $R^5$ is a halogen atom; and a suitable carrier.

8. A fungicidal composition for agricultural or horticultural use comprising, in an amount effective to control fungi in agricultural or horticultural fields, an indole-2-carboxylic acid ester derivative represented by the formula

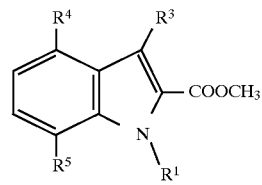

wherein $R^1$ is a hydrogen atom, $R^3$ is a hydrogen atom, $R^4$ is a halogen atom, and $R^5$ is a $C_{1-4}$alkyl group; and a suitable carrier.

* * * * *